(12) United States Patent
Pokroy et al.

(10) Patent No.: US 10,722,596 B2
(45) Date of Patent: Jul. 28, 2020

(54) CRYSTALS AS HOSTS FOR ENTRAPMENT AND SLOW RELEASE OF COMPOUNDS

(71) Applicant: TECHNION RESEARCH & DEVELOPMENT FOUNDATION LIMITED, Haifa (IL)

(72) Inventors: Boaz Pokroy, Haifa (IL); Matteo Calvaresi, Castel di Lama (IT); Giuseppe Falini, Bologna (IT); Iryna Polishchuk, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/575,763

(22) PCT Filed: May 19, 2016

(86) PCT No.: PCT/IL2016/050533
§ 371 (c)(1),
(2) Date: Nov. 20, 2017

(87) PCT Pub. No.: WO2016/185480
PCT Pub. Date: Nov. 24, 2016

(65) Prior Publication Data
US 2018/0117177 A1 May 3, 2018

Related U.S. Application Data

(60) Provisional application No. 62/164,667, filed on May 21, 2015.

(51) Int. Cl.
*A61K 47/69* (2017.01)
*A61K 31/713* (2006.01)
(Continued)

(52) U.S. Cl.
CPC ........ *A61K 47/6949* (2017.08); *A61K 9/0019* (2013.01); *A61K 31/704* (2013.01);
(Continued)

(58) Field of Classification Search
CPC ...... A61K 38/28; A61K 45/06; A61K 31/704; A61K 31/713; A61K 33/10;
(Continued)

(56) References Cited

U.S. PATENT DOCUMENTS

2005/0031591 A1* 2/2005 Hamada ................. C12N 15/85
424/93.2
2005/0282012 A1* 12/2005 Butler ..................... B01J 13/02
428/402.21

FOREIGN PATENT DOCUMENTS

CN 101428009 A 5/2009
WO 2017077539 A1 5/2017

OTHER PUBLICATIONS

Kong et al. ("Calcium carbonate microparticles used as a gene vector for delivering p53 gene into cells," in Society for Biomaterials, 2012, pp. 1-7.*

(Continued)

*Primary Examiner* — Blessing M Fubara
(74) *Attorney, Agent, or Firm* — The Roy Gross Law Firm, LLC; Roy Gross

(57) ABSTRACT

Composites comprising a metal carbonate and organic agent included within a crystal lattice of the metal carbonate are disclosed. Process of preparing the composites is also disclosed. Uses of the composites, in medicine, are also disclosed.

19 Claims, 19 Drawing Sheets

(51) Int. Cl.
  A61K 31/704    (2006.01)
  A61K 38/28     (2006.01)
  A61K 33/10     (2006.01)
  A61K 45/06     (2006.01)
  A61P 3/08      (2006.01)
  A61P 31/00     (2006.01)
  A61P 29/00     (2006.01)
  A61P 35/00     (2006.01)
  A61K 9/00      (2006.01)

(52) U.S. Cl.
  CPC ............ *A61K 31/713* (2013.01); *A61K 33/10* (2013.01); *A61K 38/28* (2013.01); *A61K 45/06* (2013.01); *A61K 47/6911* (2017.08); *A61P 3/08* (2018.01); *A61P 29/00* (2018.01); *A61P 31/00* (2018.01); *A61P 35/00* (2018.01)

(58) Field of Classification Search
  CPC ............ A61K 47/6911; A61K 47/6949; A61K 9/0019; A61K 2300/00; A61P 3/08; A61P 31/00; A61P 29/00; A61P 35/00
  See application file for complete search history.

(56) References Cited

OTHER PUBLICATIONS

Borukhin et al. ("Screening the Incorporation of Amino Acids into an Inorganic Crystalline Host: the Case of Calcite," Advanced Functional Materials, 2012, pp. 4216-4224.*

Marko Ukrainczyk et al: "Interactions of salicylic acid derivatives with calcite crystals", Journal of Colloid and Interface Science, vol. 365, 2012, pp. 296-307.

Boaz Pokroy et al: "Anisotropic lattice distortions in biogenic calcite induced by intra-crystalline organic molecules", Journal of Structural Biology, vol. 155, 2006, pp. 96-103.

Shirly Borukhin et al: "Screening the Incorporation of Amino Acids into an Inorganic Crystalline Host: the Case of Calcite", Advanced Functional Materials, vol. 22, No. 20, 2012, pp. 4216-4224.

Caiyu Peng et al: "Sustained delivery of doxorubicin by porous CaCO3 and chitosan/alginate multilayers-coated CaCO3 microparticles", Colloids and Surfaces A: Physicochemical and Engineering Aspects, vol. 353, 2010, pp. 132-139.

Haibao Peng et al: "Preparation of hierarchical mesoporous CaCO3 by a facile binary solvent approach as anticancer drug carrier for etoposide", Nanoscale Research Letters, vol. 8, No. 321, 2013, pp. 1-11.

Gleb B. Sukhorukov et al: "Porous calcium carbonate microparticles as templates for encapsulation of bioactive compounds", Journal Material Chemistry, vol. 14, No. 14, Jun. 15, 2004, pp. 2073-2081.

Wei Wei et al: "Preparation of Hierarchical Hollow CaCO3 Particles and the Application as Anticancer Drug Carrier", Journal of the American Chemical Society, vol. 130, No. 47, Nov. 4, 2008, pp. 15808-15810.

Xiangdong Kong et al: "Calcium carbonate microparticles used as a gene vector for delivering p53 gene into cancer cells", Journal of Biomedical Materials Research A, vol. 100, No. 9, Apr. 24, 2012, pp. 2312-2318.

Wefnu Lu et al: "In vitro effects of recombinant otoconin 90 upon calcite crystal growth. Significance of tertiary structure", Hearing Research; vol. 268, Issues 1-2, Sep. 1, 2010, pp. 172-183.

* cited by examiner

US 10,722,596 B2

CRYSTALS AS HOSTS FOR ENTRAPMENT AND SLOW RELEASE OF COMPOUNDS

RELATED APPLICATIONS

This application is a National Phase of PCT Patent Application No. PCT/IL2016/050533 having International filing date of May 19, 2016, which claims the benefit of priority from U.S. Provisional Patent Application No. 62/164,667, filed on May 21, 2015. The content of the above applications are all incorporated by reference in their entirety as if fully set forth herein.

FIELD OF THE INVENTION

The present invention relates to composites comprising organic agent, e.g., a drug, entrapped within crystalline lattice of a salt, processes of preparing same, and uses thereof in, for example, medicine.

BACKGROUND OF THE INVENTION

"Drug release" refers to the process in which drug solutes migrate from its position within the release modifying compound or compounds into the medium. Drug release is an important topic in the field of drug delivery for decades. With advancement in material design and engineering, novel materials with increasing complexity and more functions have been introduced into the development of drug delivery devices and systems.

In general, development of an effective drug delivery system requires understanding of the chemical and physical properties that affect i) the interaction between the drug and the micro-nano-particles (carriers), and ii) the interaction between the micro-nano-carries and the biological environment. Often, the structural characterization of the interaction between drug and carrier is missing. Dopant molecules can be either located between individual crystallites of polycrystalline materials or entrapped inside single crystals where they can mimic the stereochemical features of the host.

Molecules, macromolecules and polymers are vastly used to control drug release. Controlling drug release has direct impact on the bioefficacy, the clinical effect and often times on the quality of life of the target patient population.

There are various factors that influence drug release such as: solute diffusion, polymeric matrix swelling, and material degradation. Fick's law of diffusion provides the fundament for the description of solute transport from polymeric matrices. Fickian diffusion refers to the solute transport process in which the polymer relaxation time (tr) is much greater than the characteristic solvent diffusion time (td). When tr≈td, the macroscopic drug release becomes anomalous or non-Fickian.

Nano- and micro-particles hold great promise for controlled and targeted drug release and delivery. An ideal drug carrier should not exert harmful effects on normal cells. It should also satisfy requirements of stability, in vivo biocompatibility, and ability of targeted on-demand release. Inorganic nanomaterials may fulfill most of these requirements. Due to the simplicity of synthesis and modification, it is possible to control the particle size, shape and surface functionalization. Inorganic nanomaterials are usually made of durable and robust materials, which allow encapsulation and protection of sufficient amounts of cargos, preventing pre-leakage and damage to normal cells.

The purpose of mathematical modeling is to simplify the complex release process and to gain insight into the release mechanisms of a specific material system. However, the existing mathematical models may be insufficient in describing more complex material systems, e.g. delivery systems integrating multiple material components, or stimuli-triggered delivery systems in which the interaction with complex physiological condition is involved.

SUMMARY OF THE INVENTION

The present invention relates to composites comprising organic agent, e.g., a drug, entrapped within crystalline lattice of a salt, processes of preparing same, and uses thereof in, for example, medicine.

In one embodiment, the present invention provides a composition-of-matter comprising at least one composite, wherein the at least one composite comprises a metal carbonate salt and at least one organic agent included within a crystal lattice of the salt, wherein the at least one organic agent comprises a functional group.

In another embodiment, the metal carbonate is $CaCO_3$.

In another embodiment, the functional group is selected from the group consisting of: positively charged functional group, a negatively charged functional group, an uncharged group or neutral functional group. In another embodiment, the organic agent comprises a material selected from the group consisting of: a tumor-targeting-ligand or moiety, a drug, monoclonal antibody, SiRNA, RNA, microRNA, DNA, a plasmid, a peptide, and a protein. In another embodiment, the drug is insulin. In another embodiment, the drug is an anti-cancer and/or anti-inflammatory agent selected from the group consisting of: tetracycline, minocycline, doxorubicin, anthracycline, dichloroacetic acid, ibuprofen, phenacetin, aspirin, and tumor necrosis factor (TNF) related apoptosis inducing ligand (TRAIL). In another embodiment, the organic agent is an unstable photocleavable molecule.

In another embodiment, the disclosed composition-of-matter is soluble within a pH range of below 7.

In another embodiment, a concentration of the organic agent in the at least one composite ranges from 0.001% to 5%, by weight. In another embodiment, the concentration is about 0.1 to 0.5% by weight.

In another embodiment, the disclosed composition-of-matter comprises a plurality of the composites. In another embodiment, an average diameter of the plurality of the composites is in the range of 10 nm to 100 µm. In another embodiment, at least 80% of the composites have a diameter that varies within a range of less than 25%.

In another embodiment, the disclosed composition-of-matter is characterized by an X-Ray Powder Diffraction which is devoid of peaks at positions that correspond to the organic agent. In another embodiment, the disclosed composition-of-matter is characterized by an X-Ray Powder Diffraction exhibiting at least one peak at a position and/or width that is different from a position and/or width of a corresponding peak in an X-Ray Powder Diffraction of the metal carbonate salt. In another embodiment, the position of the at least one peak is different from the position of the corresponding peak in the X-Ray Powder Diffraction of the metal carbonate salt by at least 0.05°.

In another embodiment, the disclosed composition-of-matter is characterized by a crystal lattice exhibiting at least one cell parameter that is different from a corresponding cell parameter of a pristine crystal lattice of the metal carbonate salt. In another embodiment, the cell parameter is different from a corresponding cell parameter of a pristine crystal lattice of the metal carbonate salt by at least 0.005 Å. In another embodiment, a crystal lattice is characterized by a strain of at least $3 \times 10^{-4}$ in one or more axis thereof.

In another embodiment, the disclosed composition-of-matter is prepared by dissolving a least one organic agent in a precursor of the metal carbonate salt, thereby forming a solution, and subjecting the solution to vapors of $CO_2$ and $NH_3$.

In a further embodiment, the invention provides a pharmaceutical or cosmeceutical product, comprising: (1) at least one composite, wherein the at least one composite comprises a metal carbonate salt and at least one organic agent included within a crystal lattice of the salt, wherein the at least one organic agent comprises a functional group; and (2) a carrier. In another embodiment, the product is a pharmaceutically acceptable injectable matrix. In another embodiment, the disclosed composition-of-matter is for use in monitoring or treating a medical condition.

In a further embodiment, the invention provides a method for treating a medical condition, comprising administering to a subject in a need thereof the disclosed composition-of-matter comprising at least one composite, wherein the at least one composite comprises a metal carbonate salt and at least one organic agent included within a crystal lattice of the salt, wherein the at least one organic agent comprises a functional group.

In another embodiment, the medical condition is selected from the group consisting of: cancer, inflammatory disease, and diabetes.

In a further embodiment, the invention provides a method for extending the release period in a physiological environment of at least one organic agent comprising a functional group, the method comprising incorporating at least one organic agent in a crystal lattice of a metal carbonate salt.

In a further embodiment, the invention provides a process for preparing a composition-of-matter comprising at least one composite, the at least one composite comprising a metal carbonate salt, and at least one organic agent included within a crystal lattice of the salt. In another embodiment, the process comprises the steps of: (a) dissolving a least one organic agent in a precursor of the carbonate salt, thereby forming a solution; (b) subjecting the solution to vapors of $CO_2$ and $NH_3$. In another embodiment, the process further comprises a step of annealing the composition-of-matter. In another embodiment, the precursor of the metal carbonate salt is $CaCl_2$. In another embodiment, the vapors of $CO_2$ and $NH_3$ is produced by using a solution of $(NH_4)_2CO_3$ in a crystallization chamber.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 9C presents growth curves of MCF10A RasV12 expressing cells in complete culture medium in the presence of calcite crystals (squared) and of DOX/calcite hybrid crystals (circle). Average values±SD of (trypan blue negative) cell number from 3 independent experiments/time point.

DETAILED DESCRIPTION OF THE INVENTION

Figure 1A:
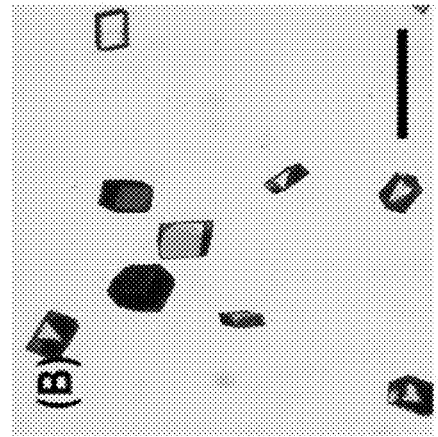
FIGS. 1A-F are micrographs of an optical microscope showing DOX/calcite hybrid crystals precipitated in the presence of different initial concentrations of DOX (DOX refers to doxorubicin): no DOX (FIG. 1A), $5 \cdot 10^{-4}$ mM (FIG. 1B), $5 \cdot 10^{-3}$ mM (FIG. 1C), $5 \cdot 10^{-2}$ mM (FIG. 1D), $5 \cdot 10^{-1}$ mM (FIG. 1E), and 5 mM (FIG. 1F). Scale bar 100 μm.
Figure 1B:
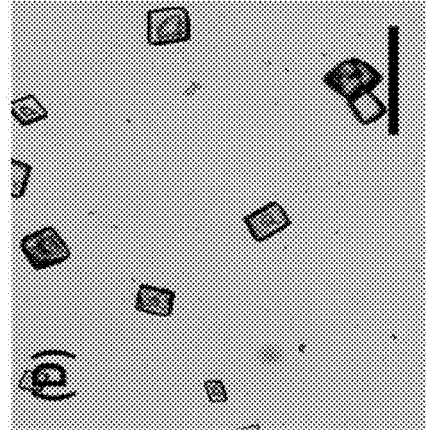
Figure 1C:
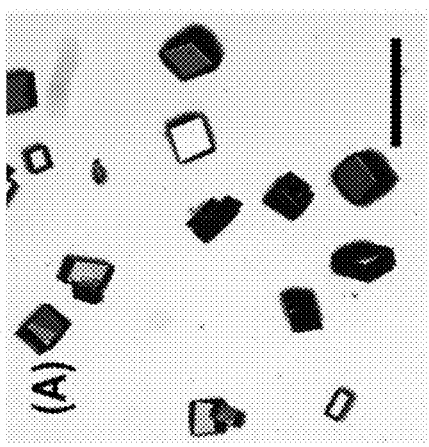
Figure 1D:
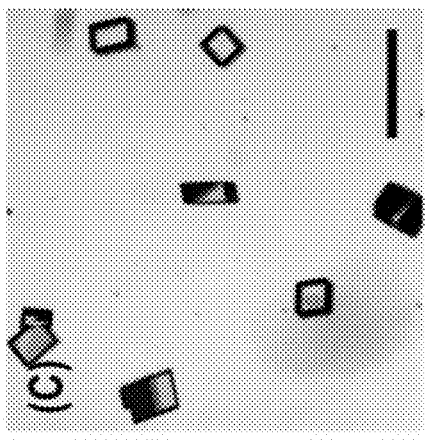
Figure 1F:
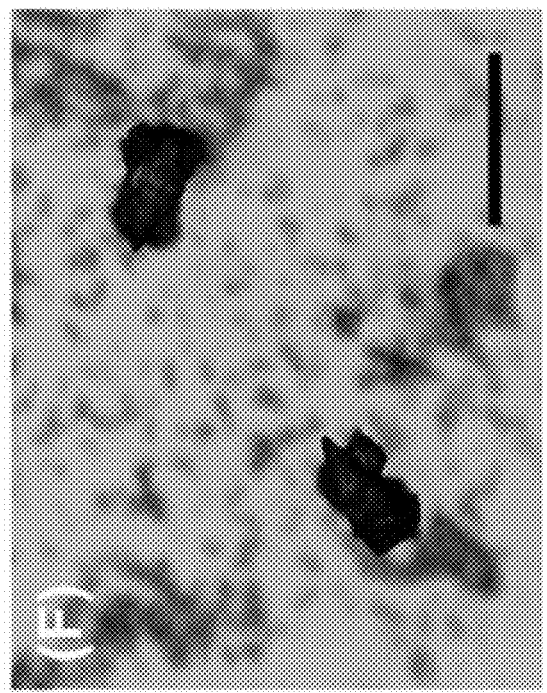
Figure 1E:
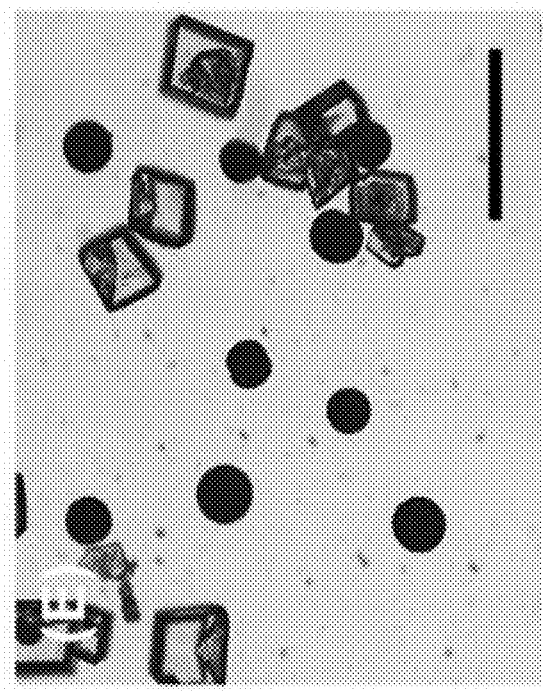
Figure 2A:
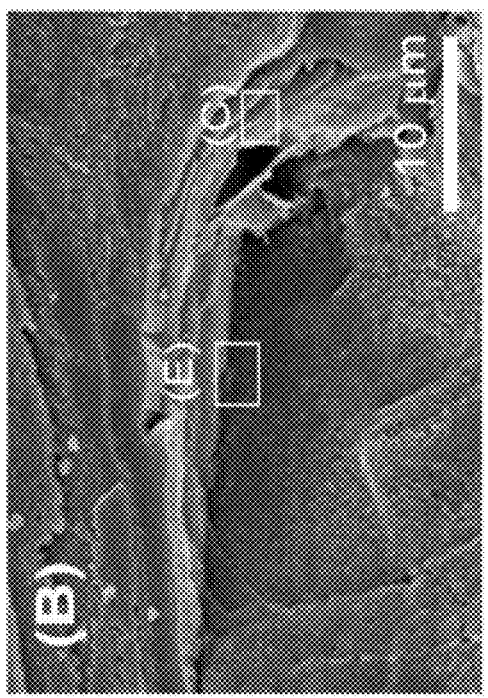
FIGS. 2A-F are micrographs of a scanning electron microscope showing DOX/calcite hybrid crystals precipitated in the presence of $5 \cdot 10^{-2}$ mM DOX. Textural details of different region of the crystal in FIG. 2A are illustrated. The rectangle indicates the region of magnification and the subscript the corresponding picture.
Figure 2B:
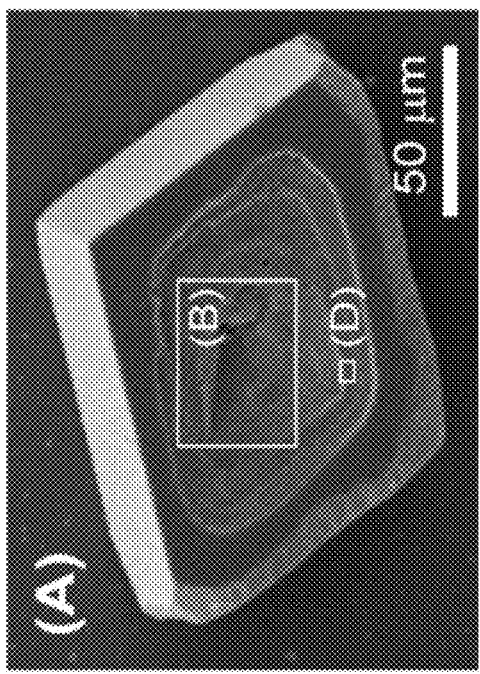
Figure 2C:
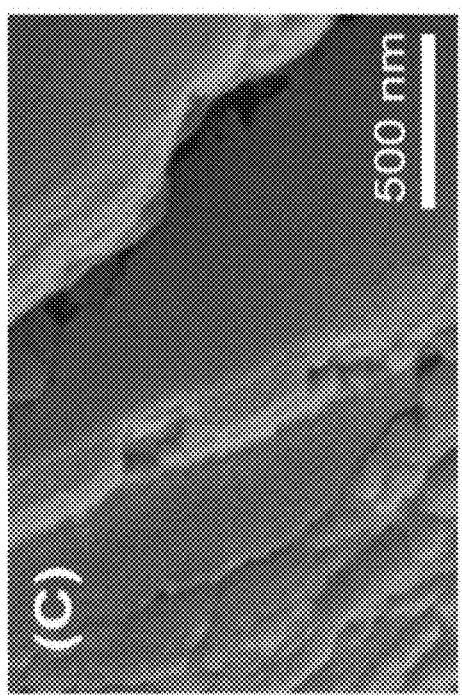
Figure 2D:
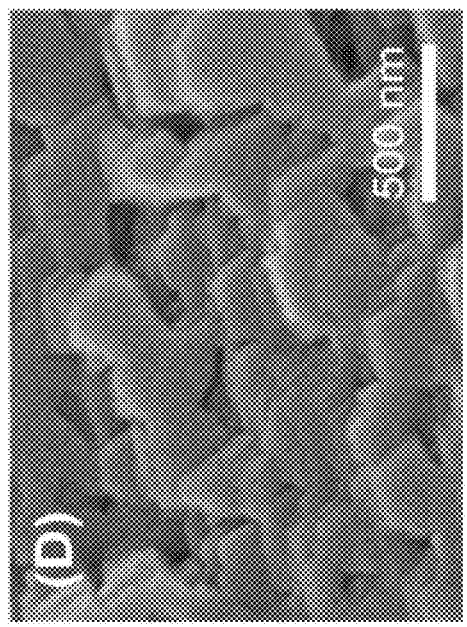
Figure 2F:
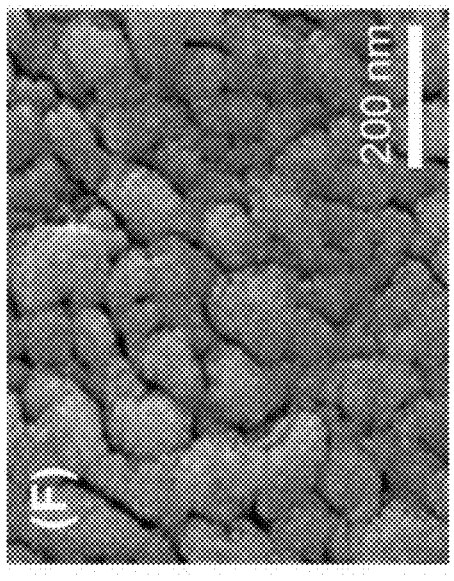
Figure 2E:
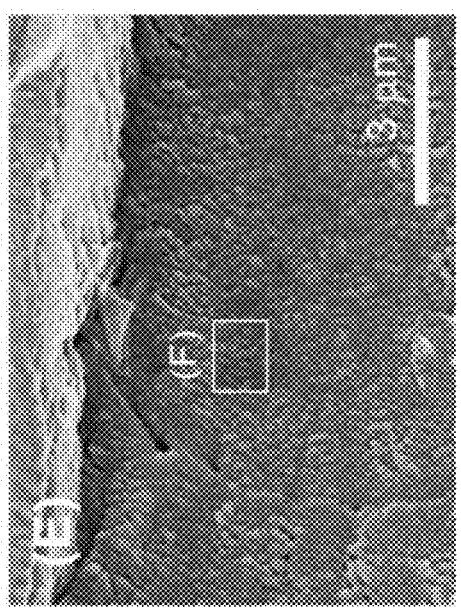

The present invention provides, in one embodiment, a composition-of-matter comprising at least one composite, wherein the at least one composite comprises a metal carbonate salt and at least one organic agent included within a crystal lattice of the salt. In some embodiments, the at least one organic agent comprises a functional group. In another embodiment, there is provided a composite, comprising a metal carbonate salt and at least one organic agent included within a crystal lattice of the salt, wherein the at least one organic agent comprises a functional group. In another embodiment, there is provided here a composition-of-matter consisting of a metal carbonate salt and an organic agent included within a crystal lattice of the metal carbonate salt. In another embodiment, a crystal lattice of the salt is single crystal. As used herein, the unit cell is the smallest component of the crystal lattice and describes the 3D arrangement of atoms in a crystal. The unit cell is represented in terms of its lattice parameters which are the lengths of the cell edges (a, b and c) and the angles between them (alpha, beta and gamma), while the positions of the atoms inside the unit cell are described by the set of atomic positions (xi, yi, zi) measured from a lattice point. X-ray Powder Diffraction (XRD) is typically used to determine the crystal arrangement of a crystal lattice.

In another embodiment, "included within" is engulfed by. In another embodiment, "included within" is entrapped. In another embodiment, "included within" is being chemically adsorbed within the crystal lattice. The inclusion of such organic agent in the crystal lattice of the metal carbonate is also referred to herein and in the art as "doping", with the organic agent being referred to as "dopant". In another embodiment, the organic agent is doped within the crystal lattice.

In another embodiment, metal carbonate is Lithium (Li) carbonate. In another embodiment, metal carbonate is Sodium (Na) carbonate. In another embodiment, metal carbonate is Potassium (K) carbonate. In another embodiment, metal carbonate is Rubidium (RB) carbonate. In another embodiment, metal carbonate is Cesium (Cs) carbonate. In another embodiment, metal carbonate is Beryllium (Be) carbonate. In another embodiment, metal carbonate is Strontium (Sr) carbonate. In another embodiment, metal carbonate is Magnesium (Mg) carbonate. In another embodiment, metal carbonate is Manganese (Mn) carbonate. In another embodiment, metal carbonate is Iron (Fe) carbonate. In another embodiment, metal carbonate is zinc (Zn) carbonate. In another embodiment, metal carbonate is Cobalt (Co) carbonate. In another embodiment, metal carbonate is nickel (Ni) carbonate. In another embodiment, metal carbonate is Copper (Cu) carbonate. In another embodiment, metal carbonate is Silver (Ag) carbonate. In another embodiment, metal carbonate is Francium (Fr) carbonate. In another embodiment, metal carbonate is $CaCO_3$.

In another embodiment, a functional group is or comprises any one of a charged functional group, a positively charged functional group, a negatively charged functional group, an uncharged group or neutral functional group. In another embodiment, a functional group is or comprises an amino acid. In another embodiment, a functional group is or comprises a carboxylic acid.

In another embodiment, at least one organic agent is doxorubicin (DOX). In another embodiment, a crystal nanoparticle (e.g., of calcium carbonate) is used as a host for DOX. In another embodiment, DOX is incorporated inside metal carbonate (e.g., $CaCO_3$) single crystals.

In another embodiment, a crystal is characterized by the presence of a rounded cavity at the center of one of the (10.4) faces. In another embodiment, the wall of the cavity is stepped, with each step formed by a flat (10.4) face and some unspecific rough riser. In another embodiment, moving toward the centre of the crystal, the thickness of the steps decreases from 400 to 600 nm to less than 200 nm. In another embodiment, the surface of the (hk.l) face shows the presence of packed spheroid nanoparticles, of 50 to 150 nm.

In another embodiment, the composition-of-matter and/or the composite is characterized by an X-Ray Powder Diffraction (XRD) which is devoid of peaks at positions that correspond to a pristine metal carbonate of the metallic element. In another embodiment, the composition-of-matter and/or the composite (or a plurality of composites) is characterized by an X-Ray Powder Diffraction exhibiting at least one peak at a position and/or width that is different from a position and/or width of a corresponding peak in an X-Ray Powder Diffraction of a pristine crystal lattice of the metal carbonate. In another embodiment, the composition-of-matter and/or the composite (or a plurality of composites) is characterized by a crystal lattice exhibiting at least one cell parameter that is different from a corresponding cell parameter of a pristine crystal lattice of the metal carbonate. Hereinthroughout, "peak position" refers to the reflection peaks along the 2 θ refractive angle axis in an XRD spectrum, and refers to the peak position at any peak intensity. The peak position is denoted by the 2 theta angle. By "devoid of peaks at positions that correspond to a pristine metal carbonate of the metallic element" it is meant that an XRD pattern of the composition-of-matter or of the composites (e.g., nanosized composite) comprised therein do not include peaks in intensity higher than 100 counts, or higher than 50 counts, which correspond to e.g., international standard values of XRD pattern of a metal carbonate of the metallic element. In another embodiment, by "devoid of" it is meant no more than 1% of the metal carbonate of organic agent, by weight. In another embodiment, by "devoid of" it is meant no more than 0.1% of the metal carbonate of organic agent, by weight. In another embodiment, by "devoid of" it is meant no more than 0.01% of the metal carbonate of the organic agent, by weight.

In one embodiment, the term "composite" include composites. In one embodiment, the term "composite" means the inclusion of an organic agent in the crystal lattice of the metal carbonate. In one embodiment, the term "composite" refers to "doping" (the state of the lattice and the organic agent) wherein the organic agent is the dopant. In one embodiment, the term "composite" refers to an organic agent doped within the crystal lattice.

In another embodiment, XRD measurements of a composition-of-mater, a composite, or of a plurality of composites as described herein exhibits a shift at a peak position of at least one peak with respect to the corresponding peak position(s) of a pristine (non-doped) metal carbonate. In another embodiment, a shift is observed in at 1 to 12 peak position(s) with respect to the corresponding peak position(s) of pristine metal carbonate. In another embodiment, a shift is observed in at 1 to 8 peak position(s) with respect to the corresponding peak position(s) of pristine metal carbonate. In another embodiment, a shift is observed in at 1 to 7 peak position(s) with respect to the corresponding peak position(s) of pristine metal carbonate. In another embodiment, a shift is observed in at 1 to 6 peak position(s) with respect to the corresponding peak position(s) of pristine metal carbonate. In another embodiment, a shift is observed in at 1 to 5 peak position(s) with respect to the corresponding peak positions of pristine metal carbonate. In another embodiment, a shift is observed in at 1 to 4 peak position(s) with respect to the corresponding peak position(s) of pristine metal carbonate. In another embodiment, a shift is observed in at least one peak position with respect to the corresponding peak positions of pristine metal carbonate. In another embodiment, a shift is observed in at least 2 peak positions with respect to the corresponding peak positions of pristine metal carbonate. In another embodiment, a shift is observed in at least 3 peak positions with respect to the corresponding peak positions of pristine metal carbonate. In another embodiment, a shift is observed in at least 4 peak positions with respect to the corresponding peak positions of pristine metal carbonate. In another embodiment, a shift is observed in at least 5 peak positions with respect to the corresponding peak positions of pristine metal carbonate. In another embodiment, a shift is observed in all peak positions with respect to the corresponding peak positions of pristine metal carbonate.

In another embodiment, a shift in the one or more peak positions is of 0.01° to 2.5°. In another embodiment, a shift in the one or more peak positions is of 0.01° to 1.5°. In another embodiment, a shift in the one or more peak positions is of 0.01° to 1°. In another embodiment, a shift in the one or more peak positions is of 0.1° to 1.5°. In another embodiment, a shift in the one or more peak positions is of 0.5° to 1.5°.

In another embodiment, a shift in the one or more peak positions is of at least 0.01°. In another embodiment, a shift in the one or more peak positions is of at least 0.02°. In another embodiment, a shift in the one or more peak positions is of at least 0.03°. In another embodiment, a shift in the one or more peak positions is of at least 0.04°. In another embodiment, a shift in the one or more peak positions is of at least 0.05°. In another embodiment, a shift in the one or more peak positions is of at least 0.06°. In another embodiment, a shift in the one or more peak positions is of at least 0.07°. In another embodiment, a shift in the one or more peak positions is of at least 0.08°. In another embodiment, a shift in the one or more peak positions is of at least 0.09°. In another embodiment, a shift in the one or more peak positions is of at least 0.1°. In another embodiment, a shift in the one or more peak positions is of at least 0.15°. In another embodiment, a shift in the one or more peak positions is of at least 0.2°. In another embodiment, a shift in the one or more peak positions is of at least 0.25°. In another embodiment, a shift in the one or more peak positions is of at least 0.3°. In another embodiment, a shift in the one or more peak positions is of at least 0.35°. In another embodiment, a shift in the one or more peak positions is of at least 0.4°. In another embodiment, a shift in the one or more peak positions is of at least 0.45°. In another embodiment, a shift in the one or more peak positions is of at least 0.5°. In another embodiment, a shift in the one or more peak positions is of at least 0.55°. In another embodiment, a shift in the one or more peak positions is of at least 0.6°. In another embodiment, a shift in the one or more peak positions is of at least 0.65°. In another embodiment, a shift in the one or more peak positions is of at least 0.7°. In another embodiment, a shift in the one or more peak positions is of at least 0.75°. In another embodiment, a shift in the one or more peak positions is of at least 0.80°. In another embodiment, a shift in the one or more peak positions is of at least 0.85°. In another embodiment, a shift in the one or more peak positions is of at least 0.9°. In another embodiment, a shift in the one or more peak positions is of at least 0.95°. In another embodiment, a shift in the one or more peak positions is of at least 1°. In another embodiment, a shift in the one or more peak positions is of at least 1.5°. In another embodiment, a shift in the one or more peak positions is of at least 2°. In another embodiment, a shift in the one or more peak positions is of at least 2.5°.

In another embodiment, a shift can be the same or different in size and/or direction, for each peak position which is shifted.

In another embodiment, an XRD measurement of a composition-of-mater or of a plurality of composites or of a composite as described herein exhibits a different peak width of at least one peak with respect to the width of corresponding peaks at corresponding positions of a pristine (non-doped) metal carbonate. In another embodiment, a different peak width is observed in at least one peak position, with respect to the corresponding peak positions of pristine metal carbonate. In another embodiment, a different peak width is observed in at least 2 peak positions, with respect to the corresponding peak positions of pristine metal carbonate. In another embodiment, a different peak width is observed in at least 3 peak positions, with respect to the corresponding peak positions of pristine metal carbonate. In another embodiment, a different peak width is observed in at least 4 peak positions, with respect to the corresponding peak positions of pristine metal carbonate. In another embodiment, a different peak width is observed in at least 5 peak positions, with respect to the corresponding peak positions of pristine metal carbonate.

In another embodiment, a different peak width is observed in 1 to 8 peak positions, with respect to the corresponding peak positions of pristine metal carbonate. In another embodiment, a different peak width is observed in 1 to 6 peak positions, with respect to the corresponding peak positions of pristine metal carbonate. In another embodiment, a different peak width is observed in 1 to 5 peak positions, with respect to the corresponding peak positions of pristine metal carbonate. In another embodiment, a different peak width is observed in 2 to 7 peak positions, with respect to the corresponding peak positions of pristine metal carbonate. In another embodiment, a different peak width is observed in 1 to 4 peak positions, with respect to the corresponding peak positions of pristine metal carbonate.

In another embodiment, a change in peak width is measured by a change in the full width at half maximum (FWHM) of the peak with respect to corresponding peaks of a pristine metal carbonate. In another embodiment, the FWHM of the peak in the one or more peak positions is broadened with respect to corresponding peaks of a pristine metal carbonate by 2% to 1000%. In another embodiment, the FWHM of the peak in the one or more peak positions is broadened with respect to corresponding peaks of a pristine metal carbonate by 2% to 500%. In another embodiment, the FWHM of the peak in the one or more peak positions is broadened with respect to corresponding peaks of a pristine metal carbonate by 2% to 100%. In another embodiment, the FWHM of the peak in the one or more peak positions is broadened with respect to corresponding peaks of a pristine metal carbonate by 5% to 50%. In another embodiment, the FWHM of the peak in the one or more peak positions is broadened with respect to corresponding peaks of a pristine metal carbonate by 10% to 80%.

In another embodiment, the FWHM of the peak in the one or more peak positions is broadened with respect to corresponding peaks of a pristine metal carbonate by at least 5%.

In another embodiment, the FWHM of the peak in the one or more peak positions is broadened with respect to corresponding peaks of a pristine metal carbonate by at least 10%. In another embodiment, the FWHM of the peak in the one or more peak positions is broadened with respect to corresponding peaks of a pristine metal carbonate by at least 11%. In another embodiment, the FWHM of the peak in the one or more peak positions is broadened with respect to corresponding peaks of a pristine metal carbonate by at least 15%. In another embodiment, the FWHM of the peak in the one or more peak positions is broadened with respect to corresponding peaks of a pristine metal carbonate by at least 20%. In another embodiment, the FWHM of the peak in the one or more peak positions is broadened with respect to corresponding peaks of a pristine metal carbonate by at least 25%. In another embodiment, the FWHM of the peak in the one or more peak positions is broadened with respect to corresponding peaks of a pristine metal carbonate by at least 30%. In another embodiment, the FWHM of the peak in the one or more peak positions is broadened with respect to corresponding peaks of a pristine metal carbonate by at least 50%. In another embodiment, the FWHM of the peak in the one or more peak positions is broadened with respect to corresponding peaks of a pristine metal carbonate by at least 100%. In another embodiment, the FWHM of the peak in the one or more peak positions is broadened with respect to corresponding peaks of a pristine metal carbonate by at least 200%. In another embodiment, the FWHM of the peak in the one or more peak positions is broadened with respect to corresponding peaks of a pristine metal carbonate by at least 500%.

In another embodiment, both shift in peak position and broadening of peak width are observed in one or more peaks, with respect to the corresponding peaks of a pristine metal carbonate. In another embodiment, both shift in peak position and broadening of peak width are observed in one or all of the peaks, with respect to the corresponding peaks of a pristine metal carbonate.

In another embodiment, a difference in the cell parameter can be a difference of any one or all of the parameters a, b and c of a cell unit, as measured by XRD measurements.

In another embodiment, one or all of the cell parameters of the composite is different from the corresponding cell parameter of the crystal lattice of a corresponding pristine metal carbonate by at least 0.001. In another embodiment, one or all of the cell parameters of the composite is different from the corresponding cell parameter of the crystal lattice of a corresponding pristine metal carbonate by at least 0.005. In another embodiment, one or all of the cell parameters of the composite is different from the corresponding cell parameter of the crystal lattice of a corresponding pristine metal carbonate by at least 0.01. In another embodiment, one or all of the cell parameters of the composite is different from the corresponding cell parameter of the crystal lattice of a corresponding pristine metal carbonate by at least 0.05. In another embodiment, one or all of the cell parameters of the composite is different from the corresponding cell parameter of the crystal lattice of a corresponding pristine metal carbonate by at least 0.05. In another embodiment, one or all of the cell parameters of the composite is different from the corresponding cell parameter of the crystal lattice of a corresponding pristine metal carbonate by at least 0.1. In another embodiment, one or all of the cell parameters of the composite is different from the corresponding cell parameter of the crystal lattice of a corresponding pristine metal carbonate by at least 0.5.

In another embodiment, one or all of the cell parameters of the composite is different from the corresponding cell parameter of the crystal lattice of a corresponding pristine metal carbonate by 0.001 to 0.9. In another embodiment, one or all of the cell parameters of the composite is different from the corresponding cell parameter of the crystal lattice of a corresponding pristine metal carbonate by 0.001 to 0.5. In another embodiment, one or all of the cell parameters of the composite is different from the corresponding cell parameter of the crystal lattice of a corresponding pristine metal carbonate by 0.01 to 0.9. In another embodiment, one or all of the cell parameters of the composite is different from the corresponding cell parameter of the crystal lattice of a corresponding pristine metal carbonate by 0.1 to 0.9.

In another embodiment, the composite is characterized by a crystal lattice strain in the c-axis and/or in the a-axis. In another embodiment, the composite is characterized by a crystal lattice strain in the c-axis and/or in the a-axis of to $1\times10^{-4}$ to $5\times10^{-3}$. In another embodiment, the composite is characterized by a crystal lattice strain in the c-axis and/or in the a-axis. In another embodiment, the composite is characterized by a crystal lattice strain in the c-axis and/or in the a-axis of $1\times10^{-4}$ to $1\times10^{-3}$. In another embodiment, the composite is characterized by a crystal lattice strain in the c-axis and/or in the a-axis. In another embodiment, the composite is characterized by a crystal lattice strain in the c-axis and/or in the a-axis of $1\times10^{-4}$ to $5\times10^{-4}$. In another embodiment, the composite is characterized by a crystal lattice strain in the c-axis and/or in the a-axis of $5\times10^{-4}$ to $8\times10^{-4}$. In another embodiment, the composite is characterized by a crystal lattice strain in the c-axis and in the a-axis.

In another embodiment, the composite is characterized by a crystal lattice strain in the c-axis and/or in the a-axis of approximately $1\times10^{-4}$. In another embodiment, the composite is characterized by a crystal lattice strain in the c-axis and/or in the a-axis of approximately $2\times10^{-4}$. In another embodiment, the composite is characterized by a crystal lattice strain in the c-axis and/or in the a-axis of approximately $3\times10^{-4}$. In another embodiment, the composite is characterized by a crystal lattice strain in the c-axis and/or in the a-axis of approximately $4\times10^{-4}$. In another embodiment, the composite is characterized by a crystal lattice strain in the c-axis and/or in the a-axis of approximately $5\times10^{-4}$. In another embodiment, the composite is characterized by a crystal lattice strain in the c-axis and/or in the a-axis of approximately $6\times10^{-4}$. In another embodiment, the composite is characterized by a crystal lattice strain in the c-axis and/or in the a-axis of approximately $7\times10^{-4}$. In another embodiment, the composite is characterized by a crystal lattice strain in the c-axis and/or in the a-axis of approximately $8\times10^{-4}$. In another embodiment, the composite is characterized by a crystal lattice strain in the c-axis and/or in the a-axis of approximately $9\times10^{-4}$. In another embodiment, the composite is characterized by a crystal lattice strain in the c-axis and/or in the a-axis of approximately $1\times10^{-3}$.

In some embodiments, the composite is characterized by a crystallite size of about 150 nm. In some embodiments, the composite is characterized by a crystallite size of about 175 nm. In some embodiments, the composite is characterized by a crystallite size of about 200 nm. In some embodiments, the composite is characterized by a crystallite size of about 250 nm. In some embodiments, the composite is characterized by a crystallite size of about 300 nm. In some embodiments, the composite is characterized by a crystallite size of about 350 nm. In some embodiments, the composite is characterized by a crystallite size of about 400 nm. In another embodiment, the term "about" means±25% of the recited value. In another embodiment, the term "about" means±10% of the recited value.

In some embodiments, the composite is characterized by a crystallite size of 50 nm to 900 nm. In some embodiments, the composite is characterized by a crystallite size of 100 nm to 600 nm. In some embodiments, the composite is characterized by a crystallite size of 150 nm to 800 nm. In some embodiments, the composite is characterized by a crystallite size of 200 nm to 400 nm.

In some embodiments, the composite is annealed. In some embodiments, the annealed composite is characterized by a crystallite size of 20 nm to 400 nm. In some embodiments, the annealed composite is characterized by a crystallite size of 50 nm to 300 nm. In some embodiments, the annealed composite is characterized by a crystallite size of 50 nm to 200 nm. In some embodiments, the annealed composite is characterized by a crystallite size of about 50 nm. In some embodiments, the annealed composite is characterized by a crystallite size of about 60 nm. In some embodiments, the annealed composite is characterized by a crystallite size of about 70 nm. In some embodiments, the annealed composite is characterized by a crystallite size of about 80 nm. In some embodiments, the annealed composite is characterized by a crystallite size of about 90 nm. In some embodiments, the annealed composite is characterized by a crystallite size of about 100 nm. In some embodiments, the annealed composite is characterized by a crystallite size of about 110 nm. In some embodiments, the annealed composite is characterized by a crystallite size of about 120 nm. In some embodiments, the annealed composite is characterized by a crystallite size of about 130 nm. In some embodiments, the annealed composite is characterized by a crystallite size of about 140 nm. In some embodiments, the annealed composite is characterized by a crystallite size of about 150 nm.

In another embodiment, the organic agent comprises or is a substance such as therapeutic agent. In another embodiment, the organic agent comprises or is a tumor-targeting-ligand or moiety. In another embodiment, the organic agent comprises or is a cell proliferation inhibitor. In another embodiment, the organic agent comprises or is a drug. In another embodiment, the organic agent comprises or is a monoclonal antibody. In another embodiment, the organic agent comprises or is a SiRNA. In another embodiment, the organic agent comprises or is an RNA. In another embodiment, the organic agent comprises or is a microRNA. In another embodiment, the organic agent comprises or is a DNA or a plasmid. In another embodiment, the organic agent comprises or is a peptide or a protein. In another embodiment, the organic agent comprises or is an anti-inflammatory agent. In another embodiment, the organic agent comprises or is an antibiotic agent. In another embodiment, the organic agent comprises or is a cardiovascular drug. In another embodiment, the organic agent comprises or is an anti-diabetic agent. In another embodiment, the organic agent comprises or is insulin. In another embodiment, the organic agent comprises or is an anti-cancer drug.

In some embodiments, the term anti-cancer drug, as used herein, refers to a drug used to treat malignancies or cancerous growths that may be used alone or in combination with other treatments. Examples of anti-cancer drugs include but are not limited to: dichloroacetic acid (DCA), doxorubicin, and retinoic acid (RA).

In another embodiment, the organic agent comprises or is doxorubicin. In another embodiment, the organic agent comprises or is dichloroacetic acid (DCA). In another embodiment, the organic agent comprises or is doxorubicin retinoic acid (RA). In another embodiment, the organic agent comprises or is anthracycline. In another embodiment, the organic agent comprises or is ibuprofen (IBU). In another embodiment, the organic agent comprises or is phenacetin (PHE). In another embodiment, the organic agent comprises or is aspirin (ASP). In another embodiment, the organic agent comprises or is a tumor necrosis factor (TNF). In another embodiment, the organic agent comprises or is tumor necrosis factor related apoptosis inducing ligand (TRAIL).

In another embodiment, the organic agent comprises or is drug-delivery system e.g., aimed to deliver active molecules to the site of action.

Non-limiting exemplary drug-delivery system comprises or is liposome.

In some embodiments, the term "liposome" refers to fully closed carrier molecules comprising a spherical lipid membrane which itself is in a liquid crystalline phase or a liquid gel phase, in which an entrapped liquid volume is contained. A variety of therapeutic agents can be entrapped in lipid vesicles, including water-soluble agents that can be stably encapsulated in the aqueous compartment of the liposome, lipophilic compounds that stably partition in the lipid phase of the vesicles, or agents that can be stably or transiently attached, conjugated, adsorbed or expressed on to the outer or inner surfaces of the liposomes, e.g., by electrostatic, covalent or hydrophobic interactions.

Delivering can be for diagnostic reasons (e.g., the liposome includes a diagnostic agent) or for treating (i.e., as a drug delivery tool, delivering a therapeutic agent).

In another embodiment, the organic agent comprises or is attached to a labeled compound. In certain embodiments, the labeled compound comprises a radioisotopic moiety. In another embodiment, the substance is carried by or via the circulatory system to the brain. In another embodiment, the substance to be carried by or via the circulatory system to the brain is a marker or a probe. In another embodiment, the substance to be carried by or via the circulatory system to the brain is a substance that can be precisely identified by radiological methods. In another embodiment, the substance is a labeled compound. In another embodiment, a marker or a probe is an agent useful in carrying out in vivo diagnostic procedures. In another embodiment, a "labeled compound" a "marker" or a "probe", are used interchangeably.

In another embodiment, the amount of labeled compound to be included in the compositions and formulations thereof, as described herein, can be readily determined by the skilled artisan in view of the state of the art and teaching herein provided and depending on the labeled compound selected and the use intended for the composition or formulation, taking into account factors specific to both the labeled compound and the individual to be diagnosed.

In another embodiment, the labeled compound is an isotope. In another embodiment, the labeled compound is a radiolabeled compound. Exemplary labeled compounds include, for example, materials comprising radioisotopes (e.g., $^3$H, $^4$C, $^{67}$Ga, $^{111}$In, $^{125}$I, $^{131}$I, $^{133}$Xe, etc.), material comprising fluorescent moieties (e.g., fluorescein, fluorescein isothiocyanate, etc.), material comprising enzyme (e.g., peroxidase, alkaline phosohatase, etc.), as well as additional labeled compounds known to those of skill in the art. In another embodiment, the labeled compound is an imaging agent for all imaging modalities. In another embodiment, the labeled compound is a contrast agent. In another embodiment, the labeled compound comprises a radionuclide or a paramagnetic metal.

In another embodiment, the selection of the labeled compound and methods used in diagnosis will depend upon the tissue (e.g., malignant or non-malignant or tissue type to be investigated. In another embodiment, the tissue is a brain tissue. In another embodiment, compositions of the invention incorporating $^{125}$I are particularly useful for identifying the presence and determining the severity (e.g., initially, during a course of treatment, after treatment) of cancer by gamma-counter.

In another embodiment, the organic agent is or comprises unstable molecules. In another embodiment unstable molecules refer to photosensitive molecules (e.g., minocycline). As used herein "photosensitive molecule" refers to a molecule that becomes more reactive when exposed to light (photons).

In another embodiment, the composition-of-matter is being water soluble within a pH of below 7. In another embodiment, the composition-of-matter is being water soluble within a pH range of below 6.5. In another embodiment, the composition-of-matter is being water soluble within a pH range of 2 to 7.

In another embodiment, the composition-of-matter is being not soluble in water within a pH 7. By "not soluble in water" it is meant, in one embodiment, that the $K_{sp}$ of the composition-of-matter in water is below $10^{-10}$, or in another embodiment below $10^{-9}$, or in another embodiment below $10^{-8}$, below $10^{-7}$, or in another embodiment below $10^{-6}$, or in another embodiment below $10^{-5}$, or in another embodiment below $10^{-4}$, or in another embodiment below $10^{-3}$, or in another embodiment below $10^{-2}$, or in another embodiment below $10^{-1}$.

In another embodiment, the concentration of the organic agent within the composite ranges from 0.001% to 5%, by weight. In another embodiment, the concentration of the organic agent within the composite ranges from 0.001% to 2%, by weight. In another embodiment, the concentration of the organic agent within the composite ranges from 0.001% to 1%, by weight. In another embodiment, the concentration of the organic agent within the composite ranges from 0.01% to 1%, by weight. In another embodiment, the concentration of the organic agent within the composite ranges from 0.001% to 0.5%, by weight. In another embodiment, the concentration of the organic agent within the composite ranges from 0.001% to 0.1%, by weight. In another embodiment, the concentration of the organic agent within the composite ranges from 0.05% to 0.5%, by weight. In another embodiment, the concentration of the organic agent within the composite ranges from 0.05% to 1%, by weight. In another embodiment, the concentration of the organic agent within the composite ranges from 0.1% to 0.5%, by weight. In another embodiment, the concentration of the organic agent within the composite ranges from 0.2% to 0.4%, by weight.

In another embodiment, a composition of the invention comprises a plurality of composites. In another embodiment, a composition of the invention comprises a plurality of composites or composite and a carrier as described hereinbelow. In another embodiment, a composition of the invention comprises a plurality of composites or composite and a stabilizer as described hereinbelow. In another embodiment, a composition of the invention comprises a plurality of composites or composite and a buffer solution. In another embodiment, a composition of the invention comprises a plurality of composites or composite dissolved within the composition. In another embodiment, a composition of the invention comprises a plurality of composites or composite and has a pH of below 7. In another embodiment, a composition of the invention comprises a plurality of composites or composite undissolved within the composition. In another embodiment, a composition of the invention comprises a plurality of composites or composite and has a pH of above 7. In another embodiment, a composition of the invention comprises a plurality of composites or composite and has a pH value of between 7.1 to 12. In another embodiment, a composition of the invention comprises a plurality of composites or composite and has a pH value of between 7.1 to 10.

In another embodiment, a composite diameter is in the range of 10 nm to 100 µm. In another embodiment, a composite diameter is in the range of 100 nm to 100 µm. In another embodiment, a composite diameter is in the range of 10 nm to 10 µm. In another embodiment, a composite diameter is in the range of 10 nm to 1 µm. In another embodiment, a composite diameter is in the range of 50 nm to 50 µm. In another embodiment, the average diameter of the plurality of the composites within a composition as described herein is in the range of 10 nm to 100 µm. In another embodiment, the average diameter of the plurality of the composites within a composition as described herein is in the range of 100 nm to 100 µm. In another embodiment, the average diameter of the plurality of the composites within a composition as described herein is in the range of 10 nm to 1 µm. In another embodiment, the average diameter of the plurality of the composites within a composition as described herein is in the range of 5 nm to 5 µm. In another embodiment, the average diameter of the plurality of the composites within a composition as described herein is in the range of 50 nm to 50 µm.

In another embodiment, a composition of the invention or a composite is characterized by an X-Ray Powder Diffraction which is devoid of peaks at positions that correspond to the organic agent. In another embodiment, a composition of the invention or a composite is characterized by an X-Ray Powder Diffraction exhibiting at least one peak at a position and/or width that is different from a position and/or width of a corresponding peak in an X-Ray Powder Diffraction of the metal carbonate salt. In another embodiment, the position of the at least one peak is different from the position of the corresponding peak in the X-Ray Powder Diffraction of the metal carbonate salt by at least 0.05°.

In another embodiment, a composition of the invention is characterized by a crystal lattice exhibiting at least one cell parameter that is different from a corresponding cell parameter of a pristine crystal lattice of the metal carbonate salt. In another embodiment, the cell parameter is different from a corresponding cell parameter of a pristine crystal lattice of the metal carbonate salt by at least 0.005 Å.

In another embodiment, the invention further provides processes and methods for preparing a composition and/or a composite as described herein. In another embodiment, a composition and/or a composite is prepared by dissolving at least one organic agent in a precursor of a metal carbonate salt, thereby forming a solution, and subjecting the solution to vapors of $CO_2$ and $NH_3$. In another embodiment, the process or method further includes a step of annealing the composition-of-matter or the composite. In another embodiment, the metal carbonate salt is $CaCO_3$. In another embodiment, the precursor of the metal carbonate salt is $CaCl_2$. In another embodiment, vapors of $CO_2$ and $NH_3$ are produced by using a solution of $(NH_4)_2CO_3$ in a crystallization chamber. The term "crystallization chamber" is known in the art and refers to a chamber adapted to crystallization of materials, typically comprising a sealed space to liquids and/or gases, and volatile solvents.

In another embodiment, a pharmaceutical or cosmeceutical (also referred to as "cosmeceutic") product comprises the composition-of-matter and/or composite as described herein. In another embodiment, a pharmaceutical or a cosmeceutical product further comprises a stabilizer. In another embodiment, a pharmaceutical or a cosmeceutical product further comprises a diluent. In another embodiment, a pharmaceutical or a cosmeceutical product further comprises a thickener. In another embodiment, a pharmaceutical or a cosmeceutical product further comprises a preservative.

In another embodiment, there is provided herein a method for treating a subject by a administering the composition-of-matter the invention. In another embodiment, the subject is afflicted with e.g., inflammation, cancer, diabetes, metabolic disease, infection, cardiovascular disease, renal disease, an endocrine pathology, a viral infection, a liver disease, or any combination thereof.

In another embodiment, there are provided methods of diagnosis comprising the steps of a) administering a composition as described herein to an individual in need thereof in an amount effective for detection, wherein the targeted composite comprises a labeled compound; and b) detecting the labeled compound. In another embodiment, the methods further comprise a step (c) comparing a level of labeled compound detected with a reference amount of the labeled compound detected at health or disease. In another embodiment, the reference amount is a threshold amount indicative of a disease.

In another embodiment, a composition comprising a composite as described herein is utilized in photo-dynamic therapy. In another embodiment, a composition comprising a composite as described herein is utilized as a drug carrier, an enhancer or both. In another embodiment, a composition comprising a composite as described herein is utilized for controlled release of drugs including a photosensitizing agent in tumors.

In another embodiment, a composition as described herein is utilized for extending the release of an organic agent as described herein. In another embodiment, a composition as described herein is utilized for extending the release of an organic agent for a total of up to one week. In another embodiment, a composition as described herein is utilized for extending the release of an organic agent for a total of up to 96 hours. In another embodiment, a composition as described herein is utilized for extending the release of an organic agent for a total of up to 72 hours. In another embodiment, a composition as described herein is utilized for extending the release of an organic agent for a total of up to 48 hours. In another embodiment, a composition as described herein is utilized for extending the release of an organic agent for a total of up to 24 hours.

In another embodiment, a method as described includes doping an organic agent within a metal carbonate lattice as described herein. In another embodiment, provided herein a method for extending the $t_{1/2}$ (half-life elimination time) of an organic agent (compared to a non-extended formulation or other known extended release formulations). In another embodiment, there is provided herein a method for minimizing elevated blood peaks and possible side-effects of an organic agent. In another embodiment, there is provided herein a method for decreasing the effective dose of an organic agent. In another embodiment, there is provided herein a method for increasing dosing interval of an organic agent. In another embodiment, there is provided herein a method for increasing $t_{max}$ of an organic agent. In another embodiment, there is provided herein a method for decreasing $C_{max}$ of an organic agent. In another embodiment, there is provided herein a method for extending elimination half-life of an organic agent. The terms $C_{max}$, $T_{max}$, and the half-life elimination time ($t_{1/2}$), are known in the kinetic art.

In another embodiment, there is provided herein a method for extending the release period in a physiological environment of at least one organic agent comprising a functional group, the method comprising incorporating at least one organic agent in a crystal lattice of a metal carbonate salt. In another embodiment, there is provided herein a method for extending the release period in a bodily fluid of at least one organic agent comprising a functional group, the method comprising incorporating (e.g., doping) at least one organic agent in a crystal lattice of a metal carbonate salt. In another embodiment, there is provided herein a method for extending the release period in fat of at least one organic agent comprising a functional group, the method comprising incorporating at least one organic agent in a crystal lattice of a metal carbonate salt. In another embodiment, there is provided herein a method for extending the release period in the blood of at least one organic agent comprising a functional group, the method comprising incorporating at least one organic agent in a crystal lattice of a metal carbonate salt.

Composition

In another embodiment, a composition of the invention comprises a solution. In another embodiment, a composition of the invention further comprises one or more pharmaceutically acceptable carriers, excipients, diluents, stabilizers, or preservatives.

In one embodiment, a composition as described herein comprises a "physiologically acceptable carrier" and "pharmaceutically acceptable carrier". In another embodiment, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

In one embodiment, a composition as described herein comprises an "excipient" which refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and/or polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the disclosed composition (also referred to as "preparation") is administered in a local rather than systemic manner, for example, via injection of the preparation directly into a specific region of a patient's body.

In another embodiment, the composition as described herein is administered via parenteral administration. In another embodiment, parenteral administration is via injection or intravenous infusion.

Oral administration of a composition of the invention, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which may not be critical for the purposes of this invention, and can be readily made by a person skilled in the art.

In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, the disclosed compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In addition, the compositions of the invention may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In another embodiment, the amount of a composition to be administered may be dependent on the subject being treated, the severity of the affliction, the manner of administration, the judgment of the prescribing physician, etc.

In another embodiment, compositions including the preparation of the present invention formulated in a compatible pharmaceutical carrier are also be prepared, placed in an appropriate container, and labeled for treatment of an indicated condition.

In another embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration (FDA) for prescription drugs or of an approved product insert.

In one embodiment, it will be appreciated that the composite or composites of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

General

As used herein the term "about", unless stated otherwise, refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods $CaCO_3$ Crystallization Experiments

In exemplary procedures, a 30×30×50 cm³ crystallization chamber was used. Two 25 mL beakers half-full of $(NH_4)_2CO_3$ (Carlo Erba) and two Petri dishes (d=8 cm) full of anhydrous $CaCl_2$ (Fluka) were placed inside the chamber. Microplates for cellular culture 20 (Microplate 24 well with Lid, IWAKI) containing a round glass cover slip in each well were used. Into each well, 750 µl of 10 mM $CaCl_2$ solutions were poured.

In the experiment with DOX, the required amount of DOX (from LC Laboratories) was dissolved in the 10 mM $CaCl_2$ solution. The micro-plate was covered with aluminum foil and a hole was made over every well. After 4 days the crystals were washed three times with milli-Q water (resistivity 18.2 NM cm at 25° C.; filtered through a 0.22 µm membrane) and then analyzed. All the experiments were conducted at room temperature. The crystallization trials of $CaCO_3$ in the different conditions were replicated three times.

Microscopic Observations

The optical microscope observations of $CaCO_3$ precipitates were made with a Leica microscope equipped with a digital camera. The SEM observations were conducted in a scansion electronic microscope using a Phenom™ microscope (FEI) for uncoated samples and a Hitachi FEG 6400 microscope for samples after coating with gold.

Atomic Absorption Spectroscopy

Atomic absorption measurements of calcium and magnesium were carried out with Perkin Elmer AAnalyst 100 flame and graphite furnace (HGA 800) spectrometer equipped with a Zeeman effect background corrector, and an automatic data processor. A 20-µl volume sample solution obtained by precipitated dissolution in 0.1 M $HNO_3$, was injected by an auto sampler. A multi element hollow cathode lamp of analytes was used as radiation source. Three measurements were carried out for each sample.

X-Ray Diffraction Analysis

X-ray diffraction analysis was performed utilizing high resolution synchrotron powder diffraction instrument: 11-BM beamline at Argonne's Advanced Photon Source (Argonne National Laboratory, Argonne, USA). Collection temperature 295.0 K, calibrated wavelength 0.413842 Å. Powders were packed and sealed into polyimide tubes and placed in the beam. Data collected from 12 crystal two-axis analyzer detector.

Confocal Laser Scanning Microscopy

Confocal laser scanning microscopy analysis was carried out on cells cultured onto glass coverslips, fixed with 3% paraformaldehyde (Sigma) in PBS and mounted with an antifade glycerol-based medium. Samples were observed with a LEICA TCS SP2 confocal laser scanning microscope (Leica Instruments) without any further modification, the fluorescence of DOX molecule was used to obtain the fluorescence images.

Measurements of the Kinetics of Drug Release

The kinetic of the drug (e.g. DOX) release was studied by UV-Vis spectroscopy (Perkin-Elmer Lambda 45). The crystals dissolution was conducted in a 0.5 M citrate buffer solution at pH 5.6 following the absorption intensity of the drug molecules at 499 nm.

Cell Culture

MCF10A cells (ATCC: crl-10317) were cultured in (1:1) Dulbecco's Modified Eagle's Medium (DMEM)/Nutrient Mixture F-12 Ham (Gibco-Life Technologies Corporation) supplemented with 5% horse serum, 20 ng/ml epidermal growth factor (EGF), 50 ng/ml cholera toxin, 500 ng/ml hydrocortisone and 0.01 mg/ml insulin (Gibco-Life Technologies Corporation). Cells were infected using a puromycin-resistant retroviral construct containing an oncogenic form of Ras (pBabe-RasV12) or using the empty vector (pBabe). Forty-eight hours post infection cells were selected using 2 µM puromycin for 4 days.

Example 1

The DOX-$CaCO_3$ Single Crystals Composite

In the present example, doxorubicin (DOX), an anthracycline drug widely used in chemotherapy, was used as a model molecule to study the entrapment in calcite crystals and its release.

Preparation of the Composite

In exemplary procedures, calcium carbonate/DOX hybrid crystal precipitation was conducted at room temperature by controlled diffusion of $CO_2$ and $NH_3$ vapors into 10 mM calcium chloride solutions containing different concentrations of DOX. The precipitation process was stopped after 4 days.

Effect of DOX Doping on the Morphology of Calcite Crystals

In the absence of DOX, only rhombohedral single crystals of calcite are precipitated. In these crystals, characterized by an average size of 50 µm, only the typical (10.4) faces are observable. The presence of DOX influenced the crystallization process as a function of its initial concentration in solution. At low concentrations, $5 \cdot 10^{-4}$ mM and $5 \cdot 10^{-3}$ mM, DOX did not affect the precipitation of calcite. At a concentration of $5 \cdot 10^{-2}$ mM the crystals became hoppered, showing holes on the {10.4} rhombohedral faces. Increasing the concentration of DOX to $5 \cdot 10^{-1}$ mM and 5 mM results both in the observation of the co-presence of spherulites with aggregated rhombohedral crystals and in the strong inhibition of the precipitation that is usually associated with the deposition of few aggregates and submicron sized particles. Calcite was the only crystalline phase detected by X-ray powder diffraction in the control experiments and in the experiments where $5 \cdot 10^{-4}$ mM, $5 \cdot 10^{-3}$ mM or $5 \cdot 10^{-2}$ mM DOX was used. When a higher concentration of DOX was used ($5 \cdot 10^{-1}$ mM and 5 mM), small amounts of vaterite co-precipitated with calcite (FIGS. 1A-F). The optimal initial concentration of DOX was $5 \cdot 10^{-2}$ mM.

The textural features of the DOX/calcite hybrid crystals were further investigated by scanning electron microscopy, as illustrated in FIG. 2A-F. Each crystal was characterized by the presence of a rounded cavity at the center of one of the {10.4} faces. The diameter of this cavity increased from inside to outside and changed among crystals. The wall of the cavity was stepped, with each step formed by a flat (10.4) face and some unspecific rough riser. Moving toward the centre of the crystal, the thickness of the steps decreases from about 500 nm to less than 200 nm. The surface of the (hk.l) face showed the presence of packed spheroid nanoparticles, of about 100 nm, on which particles of few nanometers were observed. The formation of hoppers was explained by limited diffusion of constituent ions towards the growing crystal face. In this case, formation of additional crystalline faces on the hole walls supports a mechanism of thermodynamic control of growth spiraling due to the screw dislocations induced by the DOX-calcite interaction. This aspect was further investigated by X-ray diffraction analysis.

Effect of DOX Doping on the Lattice Structure of Calcite Crystals

To examine the influence of DOX on the crystal structure of the hybrid crystals formed in the presence of the optimal concentration $5 \cdot 10^{-2}$ mM of DOX, high-resolution synchrotron powder diffraction (HRXRD) measurements were carried out on the 11-BM beamline (Argonne National Laboratory, Argonne, USA). These measurements allowed, by determination of lattice distortion parameters, to ascertain whether DOX indeed is incorporated into the calcite lattice. It was already demonstrated that when organic molecules are incorporated into an inorganic crystalline host they induce lattice distortions and lead to unique microstructures. This has been shown both in biogenic crystals as well as in bio-inspired calcite and ZnO. The procedure of the measurements has been described extensively elsewhere. In short, Rietveld analysis and line profile analysis were applied on the full diffraction patterns.

Figure 3:
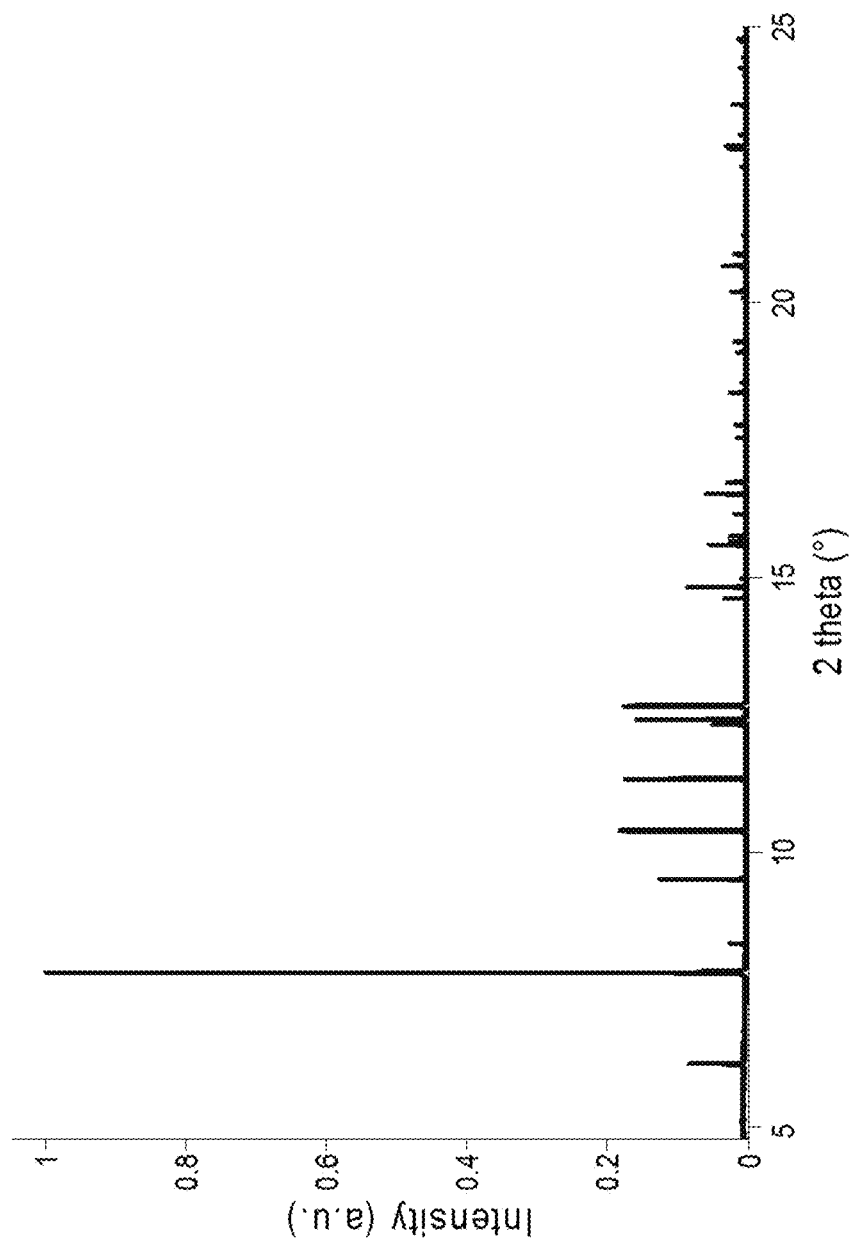
FIG. 3 is a graph showing high resolution X-ray diffraction (HRXRD) profile of the DOX/calcite hybrid crystals precipitated in the presence of $5 \times 10^{-2}$ mM DOX.

The measurements were performed on the control calcite sample, DOX/calcite hybrid sample and on the DOX/calcite hybrid sample after a mild thermal annealing at 250° C. for 2 h. Analysis of the diffraction patterns indicates a single calcite phase in all measured samples (see FIG. 3 as an example).

Figure 4:
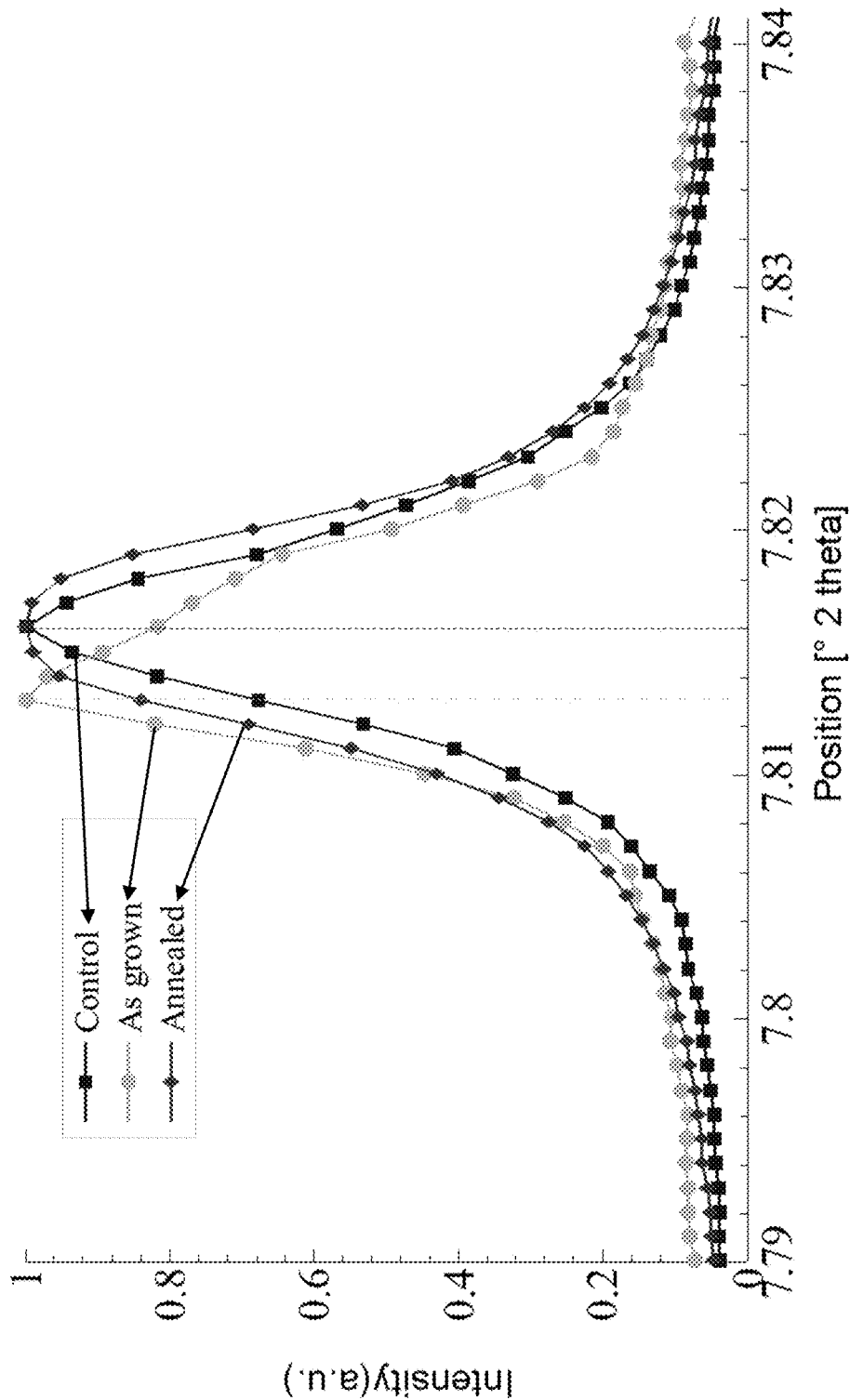
FIG. 4 is a graph showing the (104) calcite diffraction peak for control calcite, DOX/calcite hybrid crystals and after thermal annealing.

The (104) diffraction peak of DOX/calcite hybrid crystals shifts towards a smaller Bragg angle, which indicates lattice expansion compared to the control sample (see FIG. 4). This lattice distortion is due to the incorporation of DOX inside the calcite crystal. In FIG. 4 the (104) diffraction peak of the hybrid crystal is split. The splitting is due to the fact that the majority of the crystals well incorporate DOX, while some of them do not. After the mild annealing treatment the diffraction peak shifts back to that of the control sample. The lattice distortion relaxes as the organics are burnt out. The post-annealing peak becomes considerably wider, the FWHM doubles (from 0.006° to 0.0126°_) and is symmetrical. This phenomenon was also observed in previous cases such as those of biogenic crystals and for crystals that contained amino acids incorporation. The cause of the broadening after annealing has been discussed previously, but in short, it stems from the formation of new interfaces as the organics are burnt out.

Figure 5:
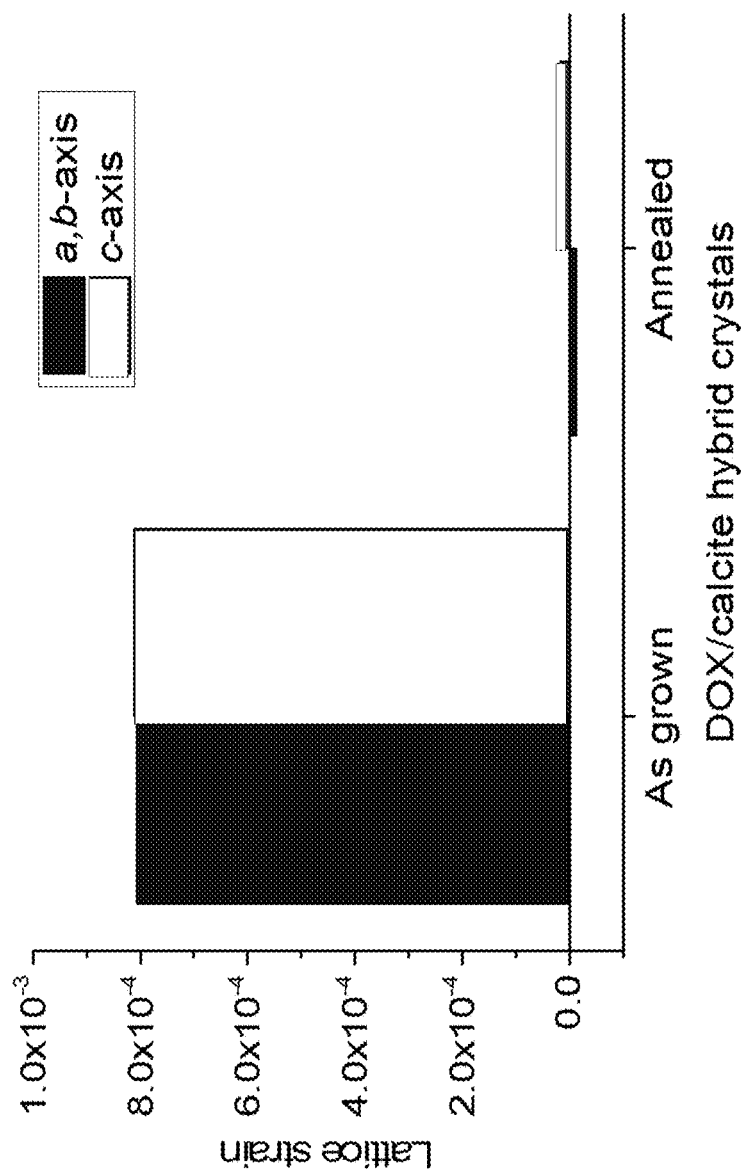
FIG. 5 presents a graph showing lattice distortions before (left bar pair) and after (right bar pair) thermal annealing for DOX/calcite hybrids compared to calcite control. In each bar pair the left bar represents a, b-axis, and the right bar represents the c-axis.

Rietveld structure refinement analysis was applied to all diffraction spectra utilizing the GSAS software and the EXPGUI interface. This analysis determined the lattice distortion, see Table 1 presenting quantitative data of lattice parameters, lattice distortions, unit cell volume and goodness of fit parameters for the Rietveld refinement fit ($\chi 2$). The strain along the a and c axes are almost equivalent ($\sim 8 \cdot 10^{-4}$) and of positive sign (i.e., expansion) (see FIG. 5). The volume change due to the incorporation is 0.24%, which may imply that the level of DOX incorporation is about 0.24% in volume.

TABLE 1

| DOX concentration in solution [mM] | a, b parameters [Å] | strain a-axis | c parameter [Å] | strain c-axis | unit cell volume [Å³] | $\chi^2$ |
|---|---|---|---|---|---|---|
| — | 4.990380 | — | 17.063950 | — | 368.03 | 4.334 |
| $5 \cdot 10^{-2}$ | 4.994405 | 8.066E−04 | 17.077791 | 8.111E−04 | 368.92 | 2.303 |
| $5 \cdot 10^{-2}$ Annealed | 4.990319 | −1.222E−05 | 17.064249 | 1.752E−05 | 368.02 | 3.754 |

Figure 6:
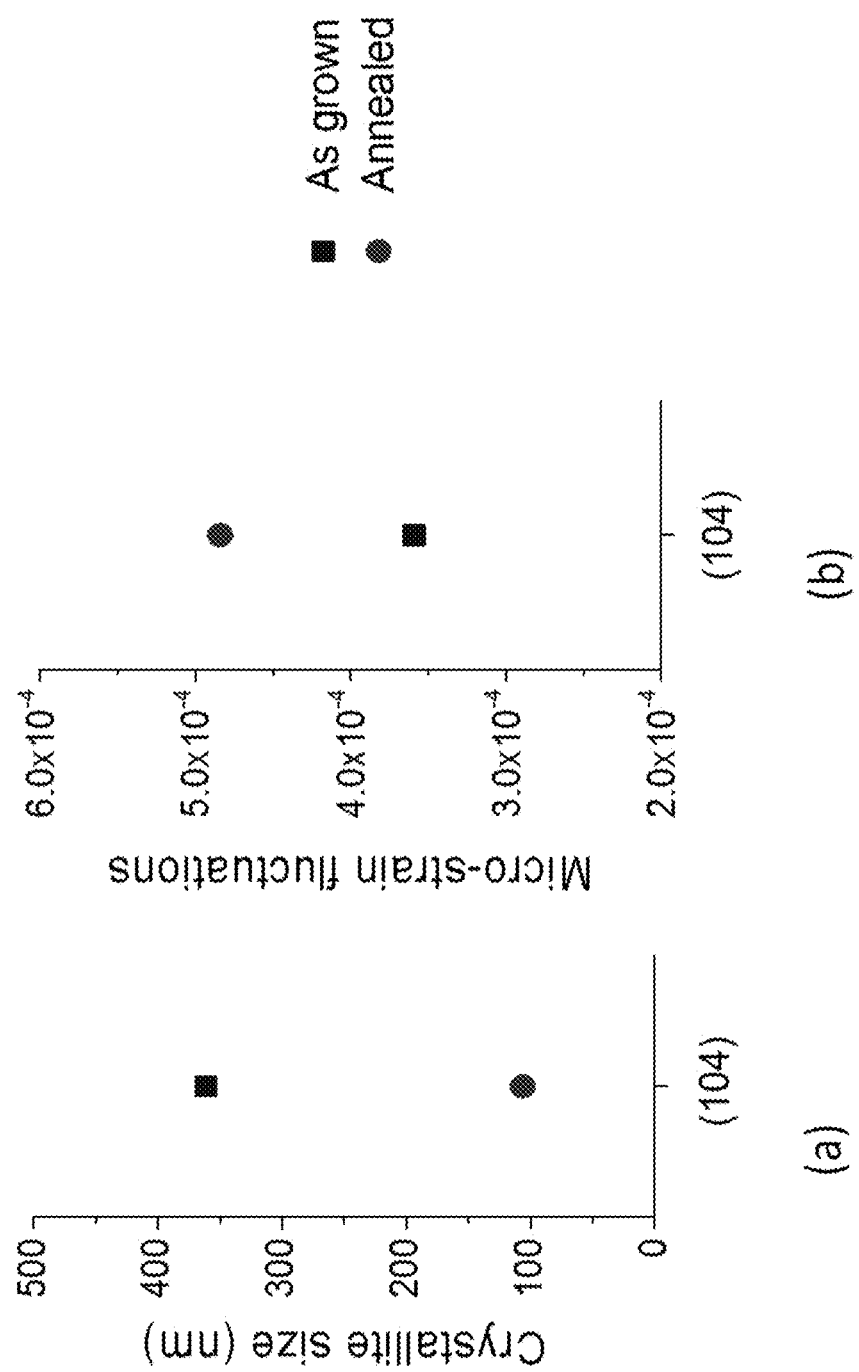
FIG. 6 presents graphs showing crystallite size (nm) and micro-strain fluctuations (left panel, designated by "a") before (square; upper in "a", lower in "b") and after (circle; upper in "b", lower in "a") thermal annealing at 250° C. for 120 min for the DOX/calcite hybrid crystals along the (104) crystallographic plane (right panel, designated by "b").
Figure 7B:
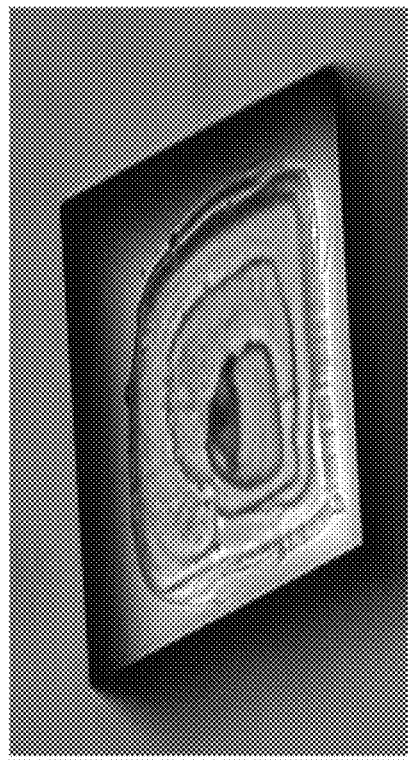
FIGS. 7A-D present micrographs showing single xy plane (FIGS. 7A-B) and 3D reconstruction (FIGS. 7C-D) of a z-stacking of a DOX/calcite crystal in fluorescence (FIGS. 7A and 7C) and reflection (FIGS. 7B and 7D) mode. The photo-detector was set up in the wavelength range of the DOX emission and of the DOX excitation.
Figure 7A:
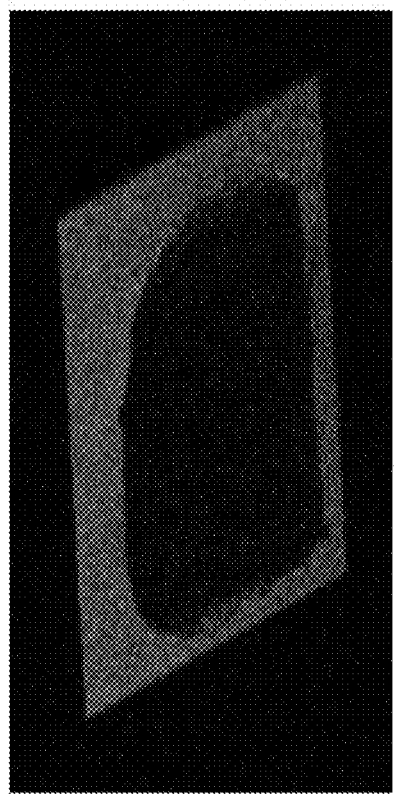
Figure 7D:
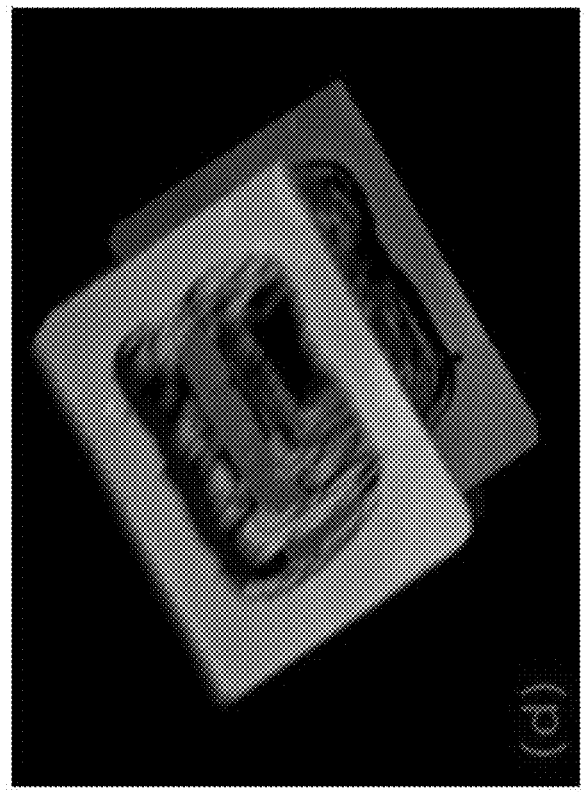
Figure 7C:
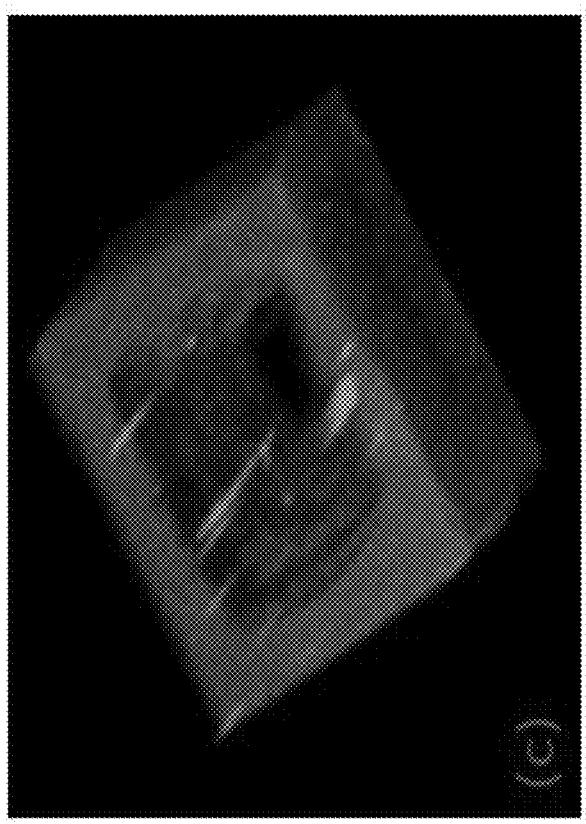

Line profile analysis was further performed on the diffraction spectra. This allowed extraction of microstructural parameters (coherence length and micro-strain fluctuations). Single diffraction peaks were fitted to a Voigt function, which enabled independent evaluation of the contributions of the Lorentzian and Gaussian types, which correlate to the coherence length (crystalline size) and micro-strain fluctuations respectively. The profile fitting was performed using the Gnuplot 4.7 interface on the most intense calcite (104) peak (FIG. 6). The results revealed noticeable reduction in crystallite size (threefold) upon annealing, which were accompanied by an increase in the averaged micro-strain fluctuations, similar to biogenic and other biomimetic crystals in which intra-crystalline organic molecules exist.

Quantification and Distribution of DOX in the DOX/Calcite Hybrid Crystals

An evaluation of the total amount of DOX adsorbed in the calcite crystal was carried out by combining UV-vis spectroscopy, for the determination of DOX, and flame atomic absorption spectroscopy, for the determination of $Ca^{2+}$. A loading of 0.3±0.1 wt % was determined.

The spatial distribution of DOX in calcite crystals was also evaluated by assessing the DOX fluorescence by confocal laser scanning microscopy. FIGS. 7A-D show the fluorescence images obtained by a z-stacking of DOX containing crystals. All longitudinal sections of the crystal display a homogeneous fluorescence intensity indicating that DOX was uniformly embedded in the crystal and that the drug is not simply adsorbed on the crystal surface. No luminescence could be detected from the reference crystal grown in the absence of DOX.

Targeted DOX Release

Figure 8:
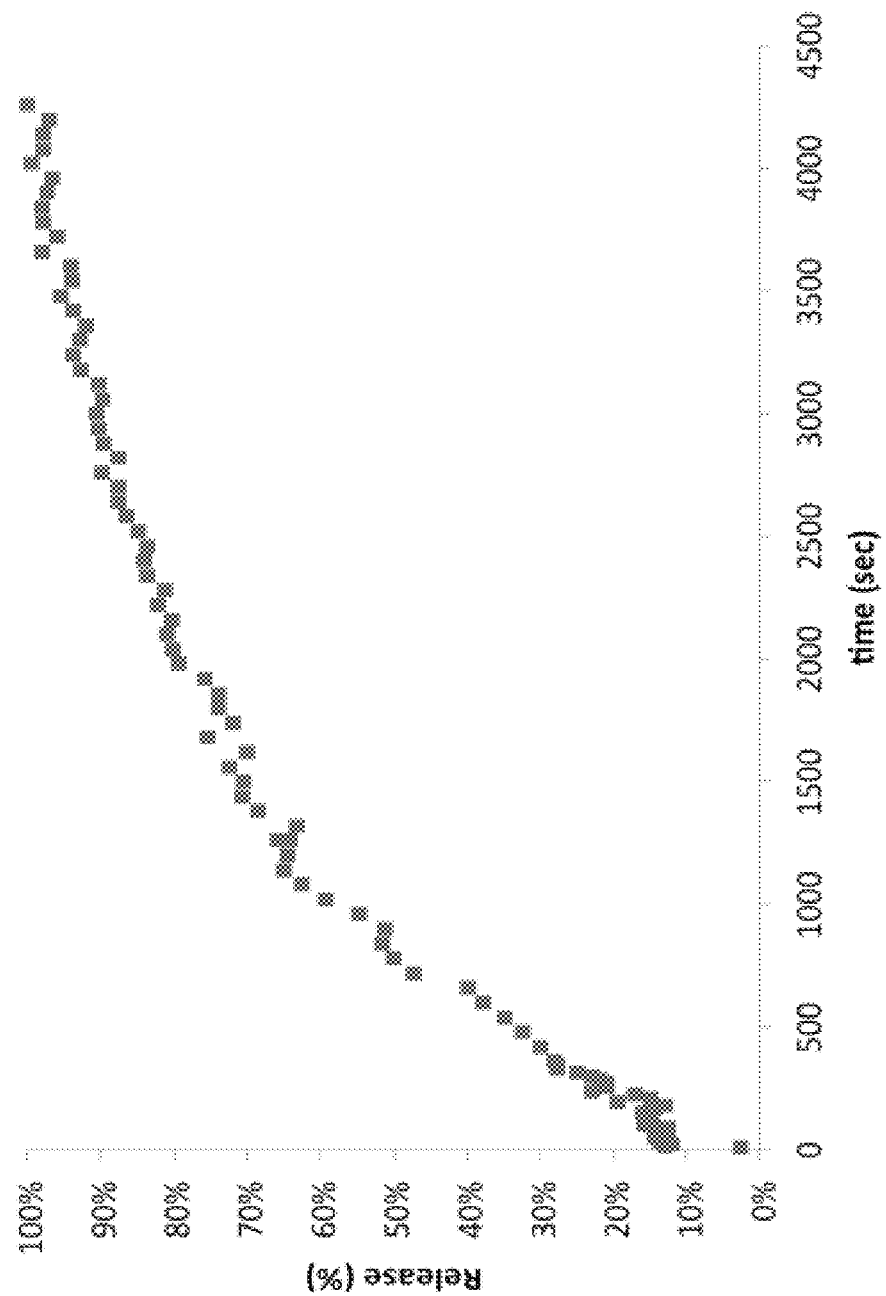
FIG. 8 is a graph showing kinetics of DOX release from DOX/calcite hybrid crystals in citrate buffer at pH 5.6.
Figure 9A:
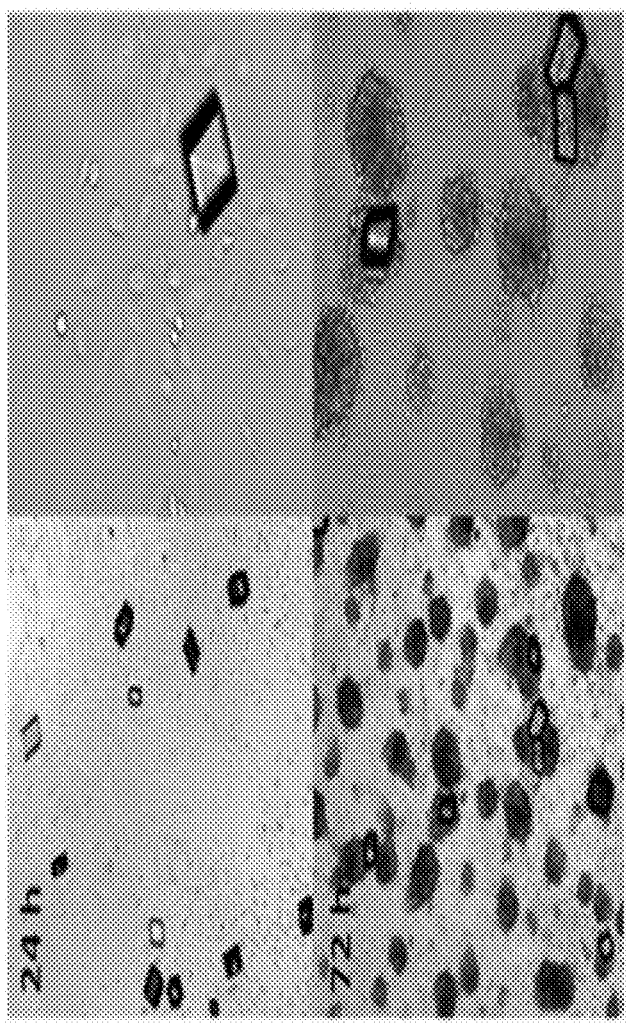
FIG. 9A-C are micrographs (9A-B) and a graph (9C) showing MCF10A RasV12 cells cultured with calcite crystals (FIG. 9A) and DOX/calcite hybrid crystals (FIG. 9B). Acquisitions were carried out at 24 (upper panels) and 72 hours (lower panels).
Figure 9B:
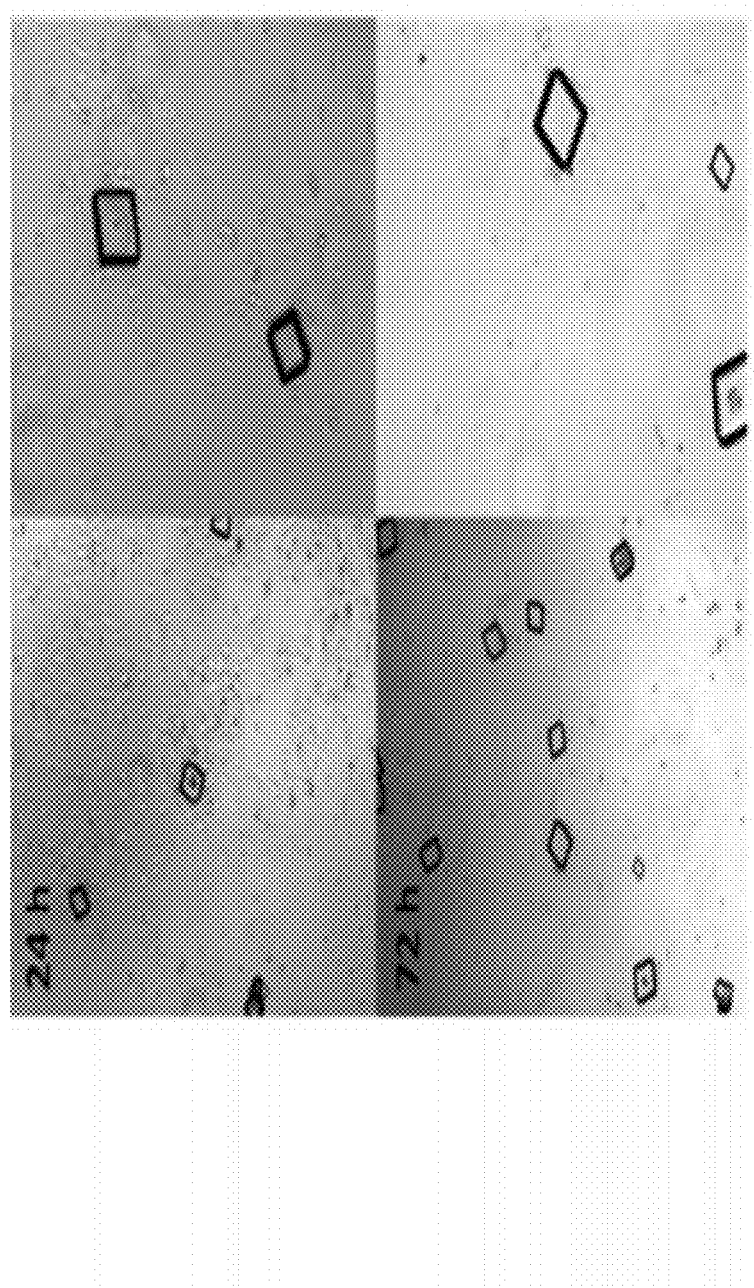
Figure 9C:
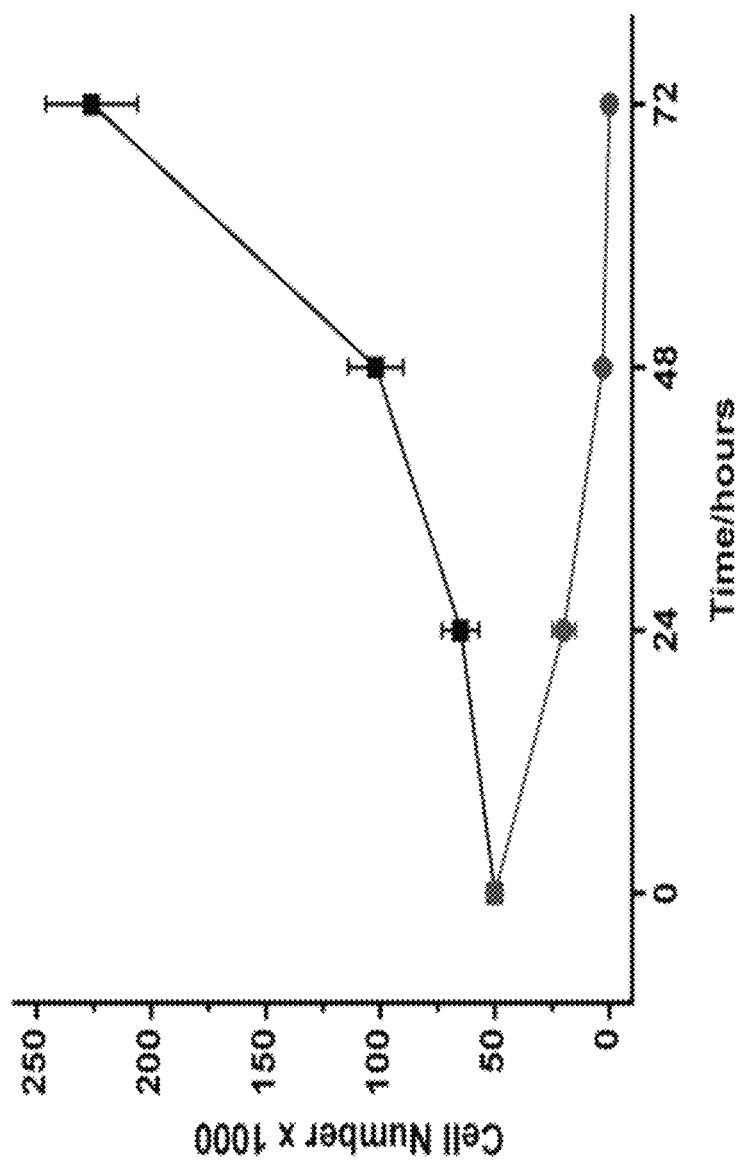

As expected, the drug carrier was pH-sensitive (FIG. 8). The DOX release kinetics from DOX/calcite crystals was measured by UV-Vis spectrophotometry in a citrate buffer at a pH of 5.6. The release of DOX was active for 72 hrs. The same measurements performed at a pH of 7.4 in PBS (phosphate buffered saline) did not show any detectable release of DOX. The drug release from the hybrid crystals is controlled by the dissolution rate of the $CaCO_3$ host crystals. In PBS no significant calcite crystals dissolution was observed (see FIGS. 9A-C) and as a consequence no UV signal at 499 nm.

In Vitro Test of the DOX/Calcite Hybrid Crystals

The pharmacological activity of DOX/calcite hybrid crystals was tested in vitro on cell cultures. The in vitro cancer model used is based on the activation of the Ras oncogenic pathway. Human non-tumorigenic breast epithelial cells (MCF10A) were subjected to retroviral (pBabe vector) infection to express the oncogenic form of Ras.

The transformed MCF10A cells were cultured in the medium in the presence of DOX/calcite hybrid crystals or calcite crystals as control. Cell growth was followed by cell counting. The contrast phase optical microscopy images at 24 h and 72 h from plating are presented in FIGS. 9A-C.

Pure calcite crystals revealed no toxic effect on MCF10A transformed cells. MCF10A cells in the presence of these crystals followed the same cell growth curve of the control cells. In contrast the DOX/calcite hybrid crystals demonstrated heavy toxic effects for the cells (FIGS. 9A-C) and after 72 hours the mortality reached 100%. This result suggests that the activity of DOX is retained in the crystal and that the DOX/calcite hybrid crystals are able to release the drug in proper concentrations. The MCF10A transformed cells induce specifically a drug release as a consequence of the cell metabolism, which decreases the local pH as a result of the increased lactate production (see FIG. 10).

Figure 10:
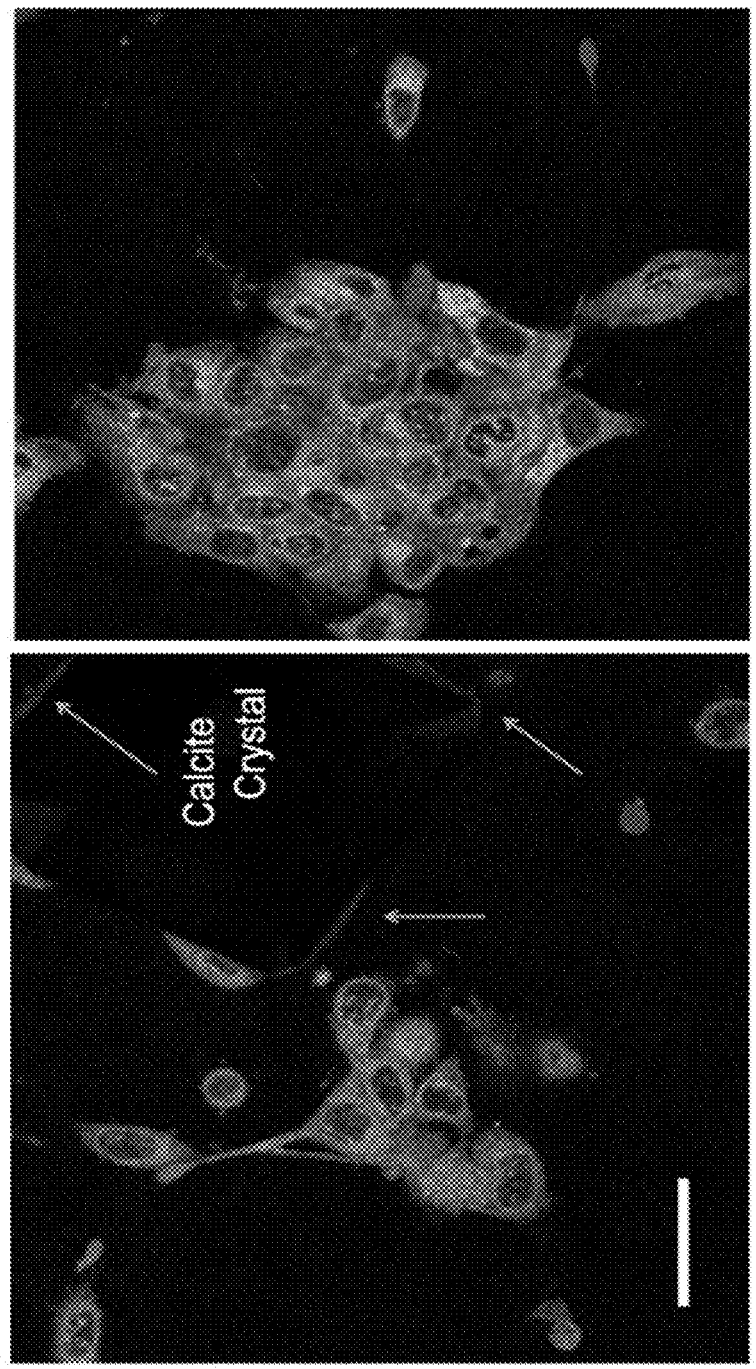
FIG. 10 presents micrographs showing uptake of DOX by cancer cells. The arrows highlight the DOX release by the DOX/calcite crystal. The arrows further indicate the periphery of the calcite crystals. In this figure DOX fluorescence is not visible in the DOX/calcite crystal, as compared to the fluorescence in FIGS. 7A and 7C, because the DOX signal of the cells is much larger than that of the crystal due to the cellular uptake that increases the DOX local concentration and saturates the signal. Scale bar 50 μm.

The DOX uptake by MCF10A RasV12 cells from the DOX/calcite hybrid crystals was assessed by following DOX fluorescence signal, using confocal laser fluorescence microscopy (FIG. 10). After 6 hrs of cell culturing in the presence of the crystals, the RasV12 MCF10A cell fluorescence images clearly indicated that the DOX molecules were inside the cells. Confocal measurements on the cells growth on pure calcite did not show the typical fluorescence of DOX. The DOX signal was clear on the dissolving surfaces of the DOX/calcite crystals (see arrows in FIG. 10).

In conclusion, a complete structural and biological characterization of $DOX/CaCO_3$ crystals as a system to specifically target drugs to particular cells or tissues is provided. This pH sensitive $CaCO_3$ solubility can release entrapped molecules only when the dissolution of the crystals occurs and allows zero-leakage of drugs at the physiological pH. The main results can be summarized in the following points: i) calcite is able to host DOX molecules efficiently; ii) the entrapment occurs along specific crystallographic directions; iii) the release of DOX is controlled by pH and occurs preferentially in proximity of the surface of cancer cells; iv) the released drug molecules are uptaken by the cancer cells, killing them.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Example 2

Single Crystals Composite of $CaCO_3$ with Other Drugs

In the present example, other molecules were incorporated in calcite crystals, and were tested in respects to their entrapment in calcite crystals.

The tested drug molecule were anti-inflammatory drugs: ibuprofen (IBU), phenacetin (PHE), aspirin (ASP), and minocycline (MIN); anticancer drugs: dichloroacetic acid (DCA), and retinoic acid (RA).

In additional example, the tested molecule was liposome which may be a promising new drug-delivery system aimed to deliver active molecules to the site of action.

$CaCO_3$ Crystallization Experiments

In exemplary procedures, a 30×30×50 $cm^3$ crystallization chamber was used. Two 25 mL beakers half-full of $(NH_4)_2CO_3$ (Carlo Erba) and two Petri dishes (d=8 cm) full of anhydrous $CaCl_2$ (Fluka) were placed inside the chamber. Microplates for cellular culture (Microplate 24 well with Lid, IWAKI) containing a round glass cover slip in each well were used. Into each well, 750 μL of 10 mM $CaCl_2$ solutions were poured. In the experiment with drugs, different amount of various drugs was dissolved in the 10 mM $CaCl_2$ solution. The micro-plate was covered with aluminum foil and a hole was made over every well. After 4 days the crystals were washed three times with milli-Q water (resistivity 18.2 MΩ cm at 25° C.; filtered through a 0.22 μm membrane) and then analyzed. All the experiments were conducted at room temperature.

Effect of the Doping on the Lattice Structure of Calcite Crystals

Rietveld structure refinement analysis was applied to all diffraction spectra utilizing the GSAS software and the EXPGUI interface. The strain along the a and c axes are shown in FIGS. 11A-C.

Figure 11A:
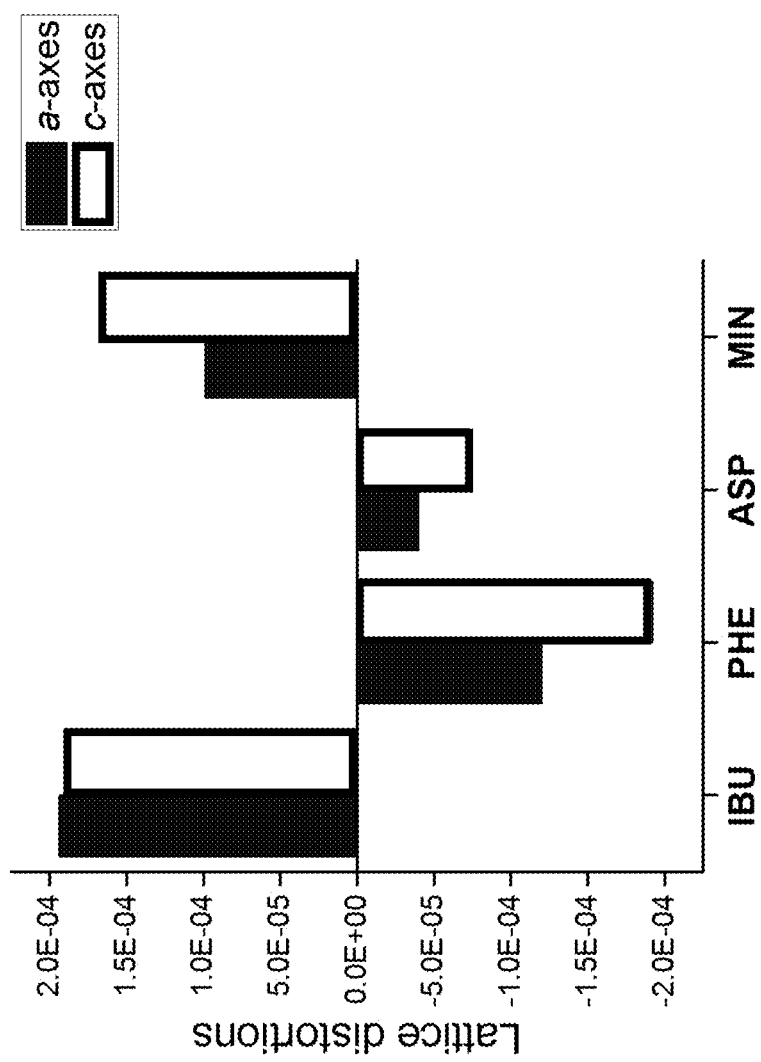
FIGS. 11A-C present bar graphs showing lattice distortions of the strain along the a (left bar in each bar pair) and c axes (right bar in each bar pair) of hybrid crystals of calcite and each of: ibuprofen (IBU), phenacetin (PHE), aspirin (ASP), and minocycline (MIN) (FIG. 11A), dichloroacetic acid (DCA), and retinoic acid (RA) (FIG. 11B), and liposome (FIG. 11C).
Figure 11B:
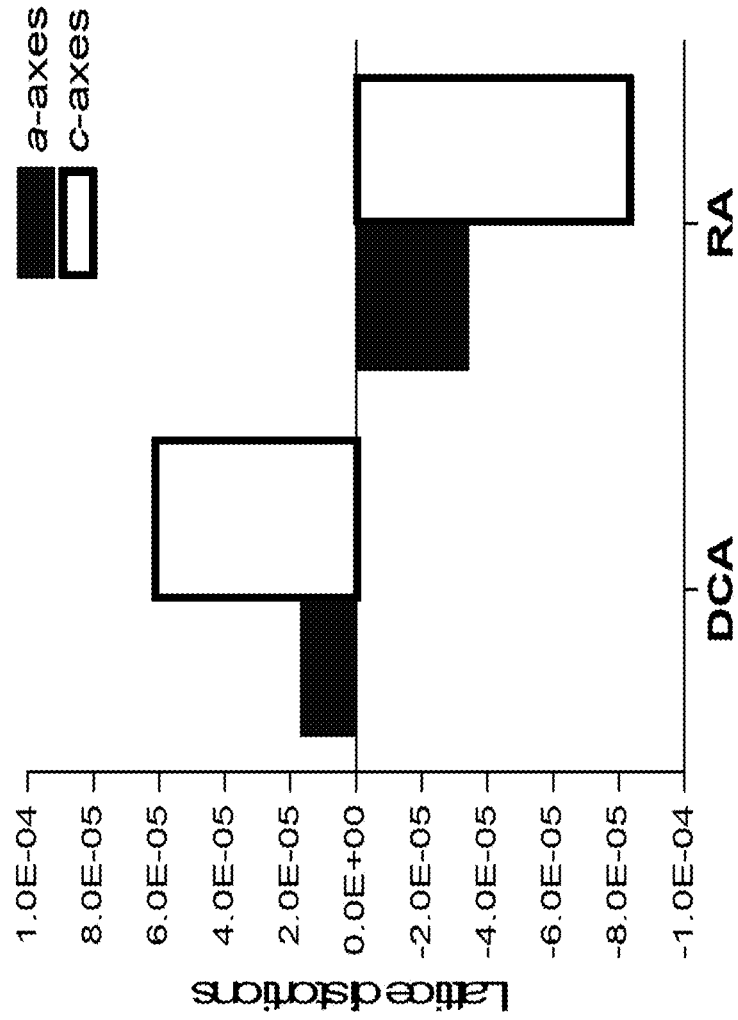
Figure 11C:
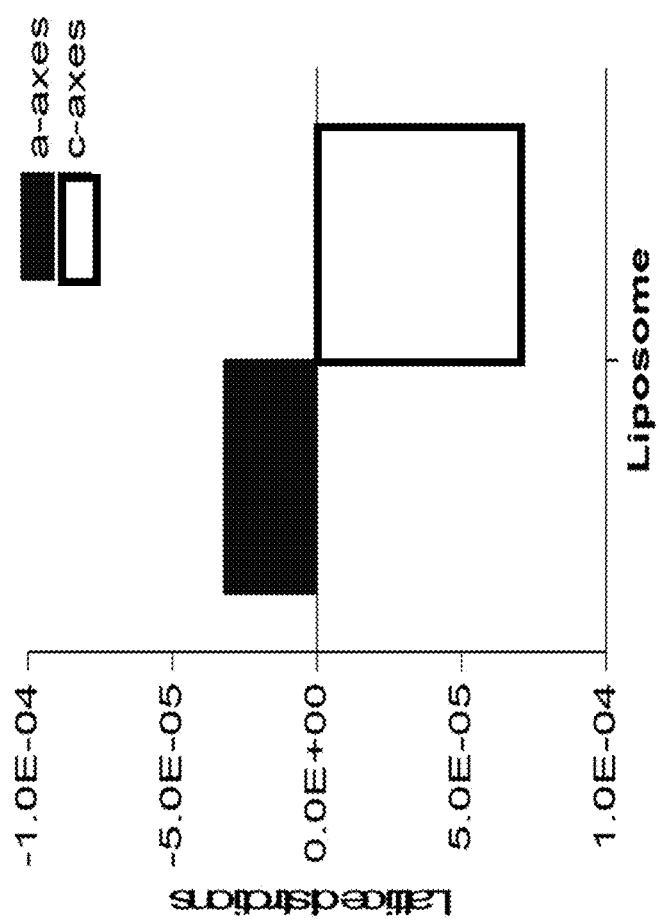

Table 2 below and FIG. 11A summarize the quantitative data of lattice distortions of calcite crystal following incorporation of IBU, PHE, ASP, or MIN.

TABLE 2

| Name | Lattice distortions a-axes | Lattice distortions c-axes |
| --- | --- | --- |
| IBU | 1.9E−04 | 1.9E−04 |
| PHE | −1.2E−04 | −1.9E−04 |
| ASP | −4.0E−05 | −7.3E−05 |
| MIN | 9.9E−05 | 1.7E−04 |

Table 3 below and FIG. 11B summarize the quantitative data of lattice distortions of calcite crystal following incorporation of DCA, RA.

TABLE 3

| Name | Lattice distortions a-axes | Lattice distortions c-axes |
|---|---|---|
| DCA | 1.9E−04 | 1.9E−04 |
| RA | −1.2E−04 | −1.9E−04 |

Table 4 below and FIG. 11C summarize the quantitative data of lattice distortions of calcite crystal following incorporation of liposome.

TABLE 4

| Name | Lattice distortions a-axes | Lattice distortions c-axes |
|---|---|---|
| Liposome | −3.2E−05 | 7.2E−05 |

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising at least one composite, said at least one composite comprises a metal carbonate salt and at least one organic agent included within a crystal lattice of said salt, wherein said at least one organic agent comprises a functional group, wherein:
    said composition-of-matter is in a form of a doped crystal;
    said at least one organic agent is selected from the group consisting of: a tumor-targeting-ligand or moiety, a drug, monoclonal antibody, SiRNA, RNA, microRNA, DNA, a plasmid, a peptide, and a protein; and
    said composition-of-matter is characterized by an X-Ray Powder Diffraction which is devoid of peaks at positions that correspond to said at least one organic agent; and wherein said crystal lattice is characterized by a strain of at least $3\times10^{-4}$ in one or more axis thereof.

2. The composition-of-matter of claim 1, wherein said metal carbonate is $CaCO_3$.

3. The composition-of-matter of claim 1, wherein said functional group is selected from the group consisting of: positively charged functional group, a negatively charged functional group, an uncharged group or neutral functional group, optionally, wherein said functional group comprises an amino acid or carboxylic acid.

4. The composition-of-matter of claim 1, wherein said drug is:
    (i) insulin, or
    (ii) an anti-cancer and/or anti-inflammatory agent selected from the group consisting of: tetracycline, minocycline, doxorubicin, anthracycline, dichloroacetic acid, ibuprofen, phenacetin, aspirin, and tumor necrosis factor (TNF) related apoptosis inducing ligand (TRAIL).

5. The composition-of-matter of claim 1, being soluble within a pH range of below 7.

6. The composition-of-matter of claim 1, wherein a concentration of said organic agent in said at least one composite ranges from 0.001% to 5%, by weight, optionally wherein said concentration is about 0.1 to 0.5% by weight.

7. The composition-of-matter of claim 1, comprising a plurality of said composites, optionally wherein an average diameter of said plurality of said composites is in the range of 10 nm to 100 μm, and optionally wherein at least 80% of said composites have a diameter that varies within a range of less than 25%.

8. The composition-of-matter of claim 1, characterized by an X-Ray Powder Diffraction exhibiting at least one peak at a position and/or width that is different from a position and/or width of a corresponding peak in an X-Ray Powder Diffraction of the metal carbonate salt, optionally, wherein said position and/or width of said at least one peak is different from said position and/or width of said corresponding peak in said X-Ray Powder Diffraction of said metal carbonate salt by at least 0.05.

9. The composition-of-matter of claim 1, characterized by a crystal lattice exhibiting at least one cell parameter that is different from a corresponding cell parameter of a pristine crystal lattice of said metal carbonate salt, optionally, wherein said cell parameter is different from a corresponding cell parameter of a pristine crystal lattice of said metal carbonate salt by at least 0.005 Å.

10. The composition-of-matter of claim 1, being prepared by dissolving a least one organic agent in a precursor of said metal carbonate salt, thereby forming a solution, and subjecting the solution to vapors of $CO_2$ and $NH_3$.

11. A pharmaceutical or cosmeceutic product, comprising the composition-of-matter of claim 1 and a carrier.

12. The pharmaceutical or cosmeceutic product of claim 11, wherein said product is a pharmaceutically acceptable injectable matrix.

13. A method for treating a medical condition, comprising administering the composition-of-matter of claim 11 to a subject in a need thereof, thereby treating a medical condition, optionally wherein said medical condition is selected from the group consisting of: cancer, inflammatory disease, and diabetes.

14. The method of claim 13, for extending the release period in a physiological environment of the at least one organic agent.

15. The method of claim 14, wherein said functional group is an amino acid or carboxylic acid.

16. The method of claim 14, wherein said organic agent comprises: a tumor-targeting-ligand or moiety, a drug, monoclonal antibody, SiRNA, RNA, microRNA, DNA, a plasmid, a peptide and a protein, optionally wherein:
    (i) said drug is insulin; or
    (ii) said drug is selected from the group consisting of: tetracycline, minocycline, doxorubicin, anthracycline, dichloroacetic acid, ibuprofen, phenacetin, aspirin, and tumor necrosis factor (TNF) related apoptosis inducing ligand (TRAIL).

17. A process for preparing a composition-of-matter comprising at least one composite, said at least one composite comprising a metal carbonate salt and at least one organic agent included within a crystal lattice of said salt, the process comprising the steps of:
    (a) dissolving a least one organic agent in a precursor of said carbonate salt, thereby forming a solution, optionally wherein said metal carbonate salt is $CaCO_3$ and optionally said precursor of said metal carbonate salt is $CaCl_2$; and (b) subjecting the solution to vapors of $CO_2$ and $NH_3$, and optionally, (c) annealing said composition-of-matter, thereby forming said composition-of-matter, wherein:

said composition-of-matter is in a form of a doped crystal;

said at least one organic agent is selected from the group consisting of: a tumor-targeting-ligand or moiety, a drug, monoclonal antibody, SiRNA, RNA, microRNA, DNA, a plasmid, a peptide, and a protein; and said composition-of-matter is characterized by an X-Ray Powder Diffraction which is devoid of peaks at positions that correspond to said at least one organic agent; and wherein said crystal lattice is characterized by a strain of at least $3 \times 10^{-4}$ in one or more axis thereof.

18. The process of claim 17, wherein said organic agent is doxorubicin.

19. The process of claim 17, wherein said vapors of $CO_2$ and $NH_3$ is produced by using a solution of $(NH_4)_2CO_3$ in a crystallization chamber.

* * * * *